(12) United States Patent
Yun et al.

(10) Patent No.: US 10,247,683 B2
(45) Date of Patent: Apr. 2, 2019

(54) MATERIAL MEASUREMENT TECHNIQUES USING MULTIPLE X-RAY MICRO-BEAMS

(71) Applicant: Sigray, Inc., Concord, CA (US)

(72) Inventors: Wenbing Yun, Walnut Creek, CA (US); Sylvia Jia Yun Lewis, San Francisco, CA (US); Janos Kirz, Berkeley, CA (US)

(73) Assignee: Sigray, Inc., Concord, CA (US)

( * ) Notice: Subject to any disclaimer, the term of this patent is extended or adjusted under 35 U.S.C. 154(b) by 0 days.

(21) Appl. No.: 15/829,947

(22) Filed: Dec. 3, 2017

(65) Prior Publication Data

US 2018/0202951 A1 Jul. 19, 2018

Related U.S. Application Data

(60) Provisional application No. 62/429,760, filed on Dec. 3, 2016.

(51) Int. Cl.
*G01N 23/223* (2006.01)
*G01N 23/2204* (2018.01)
(Continued)

(52) U.S. Cl.
CPC ..... *G01N 23/223* (2013.01); *G01N 23/20025* (2013.01); *G01N 23/2055* (2013.01); *G01N 23/2204* (2013.01)

(58) Field of Classification Search
CPC .. G01N 23/00; G01N 23/223; G01N 23/2055; G01N 23/20025; G01N 23/2204;
(Continued)

(56) References Cited

U.S. PATENT DOCUMENTS 1,203,495 A 10/1916 Coolidge
1,211,092 A 1/1917 Coolidge
(Continued)

FOREIGN PATENT DOCUMENTS

CN 102124537 A 7/2011
EP 0432568 6/1991
(Continued)

OTHER PUBLICATIONS

Dong et al., "Improving Molecular Sensitivity in X-Ray Fluorescence Molecular Imaging (XFMI) of Iodine Distribution in Mouse-Sized Phantoms via Excitation Spectrum Optimization," IEEE Access, vol. 6, pp. 56966-56976 (2018).
(Continued)

*Primary Examiner* — Jurie Yun
(74) *Attorney, Agent, or Firm* — Knobbe, Martens, Olson & Bear, LLP

(57) ABSTRACT

An x-ray interrogation system having one or more x-ray beams interrogates an object (i.e., object). A structured source producing an array of x-ray micro-sources can be imaged onto the object. Each of the one or more beams may have a high resolution, such as for example a diameter of about 15 microns or less, at the surface of the object. The illuminating one or more micro-beams can be high resolution in one dimension and/or two dimensions, and can be directed at the object to illuminate the object. The incident beam that illuminates the object has an energy that is greater than the x-ray fluorescence energy.

23 Claims, 7 Drawing Sheets

(51) Int. Cl.
  *G01N 23/20025* (2018.01)
  *G01N 23/2055* (2018.01)
(58) Field of Classification Search
  CPC ...... G01N 23/20; G01N 23/20008; A61B 6/485
  USPC .................. 378/44, 46, 49, 70, 71, 82, 90
  See application file for complete search history.

(56) References Cited

U.S. PATENT DOCUMENTS

| | | | |
|---|---|---|---|
| 1,215,116 A | 2/1917 | Coolidge | |
| 1,328,495 A | 1/1920 | Coolidge | |
| 1,355,126 A | 10/1920 | Coolidge | |
| 1,790,073 A | 1/1931 | Pohl | |
| 1,917,099 A | 7/1933 | Coolidge | |
| 1,946,312 A | 2/1934 | Coolidge | |
| 2,926,270 A | 2/1960 | Zunick | |
| 3,795,832 A | 3/1974 | Holland | |
| 4,227,112 A | 10/1980 | Waugh et al. | |
| 4,266,138 A | 5/1981 | Nelson et al. | |
| 4,426,718 A * | 1/1984 | Hayashi ............... G01N 23/207 378/72 |
| 4,523,327 A | 6/1985 | Eversole | |
| 4,573,186 A | 2/1986 | Reinhold | |
| 4,807,268 A | 2/1989 | Wittrey | |
| 4,940,319 A | 7/1990 | Ueda et al. | |
| 4,951,304 A | 8/1990 | Piestrup et al. | |
| 4,972,449 A | 11/1990 | Upadhya et al. | |
| 5,001,737 A | 3/1991 | Lewis et al. | |
| 5,008,918 A | 4/1991 | Lee et al. | |
| 5,132,997 A | 7/1992 | Kojima | |
| 5,148,462 A | 9/1992 | Spitsyn et al. | |
| 5,173,928 A | 12/1992 | Momose et al. | |
| 5,249,216 A | 9/1993 | Ohsugi et al. | |
| 5,276,724 A | 1/1994 | Kumasaka et al. | |
| 5,602,899 A | 2/1997 | Larson | |
| 5,604,782 A | 2/1997 | Cash, Jr. | |
| 5,629,969 A | 5/1997 | Koshishiba | |
| 5,657,365 A | 8/1997 | Yamamoto et al. | |
| 5,682,415 A | 10/1997 | O'Hara | |
| 5,715,291 A | 2/1998 | Momose | |
| 5,729,583 A | 3/1998 | Tang et al. | |
| 5,768,339 A | 6/1998 | O'Hara | |
| 5,772,903 A | 6/1998 | Hirsch | |
| 5,778,039 A | 7/1998 | Hossain | |
| 5,812,629 A | 9/1998 | Clauser | |
| 5,825,848 A | 10/1998 | Virshup et al. | |
| 5,832,052 A | 11/1998 | Hirose et al. | |
| 5,857,008 A | 1/1999 | Reinhold | |
| 5,878,110 A | 3/1999 | Yamamoto et al. | |
| 5,881,126 A | 3/1999 | Momose | |
| 5,912,940 A | 6/1999 | O'Hara | |
| 5,930,325 A | 7/1999 | Momose | |
| 6,108,397 A | 8/2000 | Cash, Jr. | |
| 6,108,398 A | 8/2000 | Mazor et al. | |
| 6,125,167 A | 9/2000 | Morgan | |
| 6,278,764 B1 | 8/2001 | Barbee, Jr. et al. | |
| 6,359,964 B1 | 3/2002 | Kogan | |
| 6,377,660 B1 | 4/2002 | Ukita et al. | |
| 6,381,303 B1 | 4/2002 | Vu et al. | |
| 6,389,100 B1 | 5/2002 | Verman et al. | |
| 6,430,254 B2 | 8/2002 | Wilkins | |
| 6,442,231 B1 | 8/2002 | O'Hara | |
| 6,456,688 B1 | 9/2002 | Taguchi et al. | |
| 6,463,123 B1 | 10/2002 | Korenev | |
| 6,487,272 B1 | 11/2002 | Kutsuzawa | |
| 6,504,902 B2 | 1/2003 | Iwasaki et al. | |
| 6,507,388 B2 | 1/2003 | Burghoorn | |
| 6,553,096 B1 | 4/2003 | Zhou et al. | |
| 6,560,313 B1 | 5/2003 | Harding et al. | |
| 6,560,315 B1 | 5/2003 | Price et al. | |
| 6,707,883 B1 | 3/2004 | Tiearney et al. | |
| 6,711,234 B1 | 3/2004 | Loxley et al. | |
| 6,811,612 B2 | 11/2004 | Gruen et al. | |
| 6,815,363 B2 | 11/2004 | Yun et al. | |
| 6,829,327 B1 | 12/2004 | Chen | |
| 6,847,699 B2 | 1/2005 | Rigali et al. | |
| 6,850,598 B1 | 2/2005 | Fryda et al. | |
| 6,870,172 B1 | 3/2005 | Mankos et al. | |
| 6,885,503 B2 | 4/2005 | Yun et al. | |
| 6,914,723 B2 | 7/2005 | Yun et al. | |
| 6,917,472 B1 | 7/2005 | Yun et al. | |
| 6,947,522 B2 | 9/2005 | Wilson et al. | |
| 6,975,703 B2 | 12/2005 | Wilson et al. | |
| 7,003,077 B2 | 2/2006 | Jen et al. | |
| 7,015,467 B2 | 3/2006 | Maldonado et al. | |
| 7,023,955 B2 | 4/2006 | Chen et al. | |
| 7,057,187 B1 | 6/2006 | Yun et al. | |
| 7,079,625 B2 | 7/2006 | Lenz | |
| 7,095,822 B1 | 8/2006 | Yun | |
| 7,110,503 B1 | 9/2006 | Kumakhov | |
| 7,119,953 B2 | 10/2006 | Yun et al. | |
| 7,130,375 B1 | 10/2006 | Yun et al. | |
| 7,170,969 B1 | 1/2007 | Yun et al. | |
| 7,180,979 B2 | 2/2007 | Momose | |
| 7,180,981 B2 | 2/2007 | Wang | |
| 7,183,547 B2 | 2/2007 | Yun et al. | |
| 7,215,736 B1 | 5/2007 | Wang et al. | |
| 7,215,741 B2 | 5/2007 | Ukita et al. | |
| 7,218,700 B2 | 5/2007 | Huber et al. | |
| 7,218,703 B2 | 5/2007 | Yada et al. | |
| 7,221,731 B2 | 5/2007 | Yada et al. | |
| 7,245,696 B2 | 7/2007 | Yun et al. | |
| 7,268,945 B2 | 9/2007 | Yun et al. | |
| 7,286,640 B2 | 10/2007 | Yun et al. | |
| 7,297,959 B2 | 11/2007 | Yun et al. | |
| 7,298,826 B2 | 11/2007 | Inazuru | |
| 7,330,533 B2 | 2/2008 | Sampayon | |
| 7,346,148 B2 | 3/2008 | Ukita | |
| 7,346,204 B2 | 3/2008 | Ito | |
| 7,359,487 B1 | 4/2008 | Newcome | |
| 7,365,909 B2 | 4/2008 | Yun et al. | |
| 7,365,918 B1 | 4/2008 | Yun et al. | |
| 7,382,864 B2 | 6/2008 | Hebert et al. | |
| 7,388,942 B2 | 6/2008 | Wang et al. | |
| 7,394,890 B1 | 7/2008 | Wang et al. | |
| 7,400,704 B1 | 7/2008 | Yun et al. | |
| 7,406,151 B1 | 7/2008 | Yun | |
| 7,412,024 B1 | 8/2008 | Yun et al. | |
| 7,412,030 B1 | 8/2008 | O'Hara | |
| 7,412,131 B2 | 8/2008 | Lee et al. | |
| 7,414,787 B2 | 8/2008 | Yun et al. | |
| 7,433,444 B2 | 10/2008 | Baumann | |
| 7,443,953 B1 | 10/2008 | Yun et al. | |
| 7,453,981 B2 | 11/2008 | Baumann | |
| 7,463,712 B2 | 12/2008 | Zhu et al. | |
| 7,486,770 B2 | 2/2009 | Baumann | |
| 7,492,871 B2 | 2/2009 | Popescu | |
| 7,499,521 B2 | 3/2009 | Wang et al. | |
| 7,522,698 B2 | 4/2009 | Popescu | |
| 7,522,707 B2 | 4/2009 | Steinlage et al. | |
| 7,522,708 B2 | 4/2009 | Heismann | |
| 7,529,343 B2 | 5/2009 | Safai et al. | |
| 7,532,704 B2 | 5/2009 | Hempel | |
| 7,551,719 B2 | 6/2009 | Yokhin et al. | |
| 7,551,722 B2 | 6/2009 | Ohshima et al. | |
| 7,561,662 B2 | 7/2009 | Wang et al. | |
| 7,564,941 B2 | 7/2009 | Baumann | |
| 7,583,789 B1 | 9/2009 | Macdonald et al. | |
| 7,601,399 B2 | 10/2009 | Barnola et al. | |
| 7,639,786 B2 | 12/2009 | Baumann | |
| 7,646,843 B2 | 1/2010 | Popescu et al. | |
| 7,672,433 B2 | 3/2010 | Zhong et al. | |
| 7,680,243 B2 | 3/2010 | Yokhin et al. | |
| 7,787,588 B1 | 8/2010 | Yun et al. | |
| 7,796,725 B1 | 9/2010 | Yun et al. | |
| 7,796,726 B1 | 9/2010 | Gendreau et al. | |
| 7,800,072 B2 | 9/2010 | Yun et al. | |
| 7,813,475 B1 | 10/2010 | Wu et al. | |
| 7,817,777 B2 | 10/2010 | Baumann et al. | |
| 7,864,426 B2 | 1/2011 | Yun et al. | |
| 7,864,922 B2 | 1/2011 | Kawabe | |
| 7,873,146 B2 | 1/2011 | Okunuki et al. | |
| 7,876,883 B2 | 1/2011 | O'Hara | |
| 7,889,838 B2 | 2/2011 | David et al. | |

(56) References Cited

U.S. PATENT DOCUMENTS

| | | |
|---|---|---|
| 7,889,844 B2 | 2/2011 | Okunuki et al. |
| 7,914,693 B2 | 3/2011 | Jeong et al. |
| 7,920,673 B2 | 4/2011 | Lanza et al. |
| 7,920,676 B2 | 4/2011 | Yun et al. |
| 7,924,973 B2 | 4/2011 | Kottler et al. |
| 7,929,667 B1 | 4/2011 | Zhuang et al. |
| 7,945,018 B2 | 5/2011 | Heismann |
| 7,949,092 B2 | 5/2011 | Brons |
| 7,949,095 B2 | 5/2011 | Ning |
| 7,974,379 B1 | 7/2011 | Case et al. |
| 7,983,381 B2 | 7/2011 | David et al. |
| 7,991,120 B2 | 8/2011 | Okunuki et al. |
| 8,005,185 B2 | 8/2011 | Popescu |
| 8,009,796 B2 | 8/2011 | Popescu |
| 8,041,004 B2 | 10/2011 | David |
| 8,036,341 B2 | 11/2011 | Lee |
| 8,058,621 B2 | 11/2011 | Kommareddy |
| 8,068,579 B1 | 11/2011 | Yun et al. |
| 8,073,099 B2 | 12/2011 | Niu et al. |
| 8,094,784 B2 | 1/2012 | Morton |
| 8,139,716 B2 | 3/2012 | Okunuki et al. |
| 8,184,771 B2 | 5/2012 | Murakoshi |
| 8,208,602 B2 | 6/2012 | Lee |
| 8,208,603 B2 | 6/2012 | Sato |
| 8,243,879 B2 | 8/2012 | Itoh et al. |
| 8,243,884 B2 | 8/2012 | Rödhammer et al. |
| 8,280,000 B2 | 10/2012 | Takahashi |
| 8,306,183 B2 | 11/2012 | Koehler |
| 8,306,184 B2 | 11/2012 | Chang et al. |
| 8,351,569 B2 | 1/2013 | Baker |
| 8,351,570 B2 | 1/2013 | Nakamura |
| 8,353,628 B1 | 1/2013 | Yun et al. |
| 8,360,640 B2 | 1/2013 | Reinhold |
| 8,374,309 B2 | 2/2013 | Donath |
| 8,406,378 B2 | 3/2013 | Wang et al. |
| 8,416,920 B2 | 4/2013 | Okumura et al. |
| 8,422,633 B2 | 4/2013 | Lantz et al. |
| 8,451,975 B2 | 5/2013 | Tada |
| 8,422,637 B2 | 6/2013 | Okunuki et al. |
| 8,509,386 B2 | 8/2013 | Lee et al. |
| 8,520,803 B2 | 8/2013 | Behling |
| 8,526,575 B1 | 9/2013 | Yun et al. |
| 8,532,257 B2 | 9/2013 | Mukaide et al. |
| 8,553,843 B2 | 10/2013 | Drory |
| 8,559,597 B2 | 10/2013 | Chen et al. |
| 8,565,371 B2 | 10/2013 | Bredno |
| 8,576,983 B2 | 11/2013 | Baeumer |
| 8,591,108 B2 | 11/2013 | Tada |
| 8,602,648 B1 | 12/2013 | Jacobsen et al. |
| 8,632,247 B2 | 1/2014 | Ishii |
| 8,666,024 B2 | 3/2014 | Okunuki et al. |
| 8,666,025 B2 | 3/2014 | Klausz |
| 8,699,667 B2 | 4/2014 | Steinlage et al. |
| 8,735,844 B1 | 5/2014 | Khaykovich et al. |
| 8,737,565 B1 | 5/2014 | Lyon et al. |
| 8,744,048 B2 | 6/2014 | Lee et al. |
| 8,755,487 B2 | 6/2014 | Kaneko |
| 8,767,915 B2 | 7/2014 | Stutman |
| 8,767,916 B2 | 7/2014 | Hashimoto |
| 8,781,069 B2 | 7/2014 | Murakoshi |
| 8,824,629 B2 | 9/2014 | Ishii |
| 8,831,174 B2 | 9/2014 | Kohara |
| 8,831,175 B2 | 9/2014 | Silver et al. |
| 8,831,179 B2 | 9/2014 | Adler et al. |
| 8,855,265 B2 | 10/2014 | Engel |
| 8,861,682 B2 | 10/2014 | Okunuki et al. |
| 8,903,042 B2 | 12/2014 | Ishii |
| 8,995,622 B2 | 3/2015 | Adler et al. |
| 9,001,967 B2 | 4/2015 | Baturin |
| 9,008,278 B2 | 4/2015 | Lee et al. |
| 9,016,943 B2 | 4/2015 | Jacobsen et al. |
| 9,020,101 B2 | 4/2015 | Omote et al. |
| 9,129,715 B2 | 9/2015 | Adler et al. |
| 9,329,141 B2 | 5/2016 | Stutman |
| 9,357,975 B2 | 6/2016 | Baturin |
| 9,390,881 B2 | 7/2016 | Yun et al. |
| 9,439,613 B2 | 9/2016 | Stutman |
| 9,448,190 B2 | 9/2016 | Yun et al. |
| 9,449,781 B2 | 9/2016 | Yun et al. |
| 9,543,109 B2 | 1/2017 | Yun et al. |
| 9,570,265 B1 | 2/2017 | Yun et al. |
| 9,594,036 B2 | 3/2017 | Yun et al. |
| 9,632,040 B2 | 4/2017 | Stutman |
| 9,719,947 B2 | 8/2017 | Yun et al. |
| 9,823,203 B2 | 11/2017 | Yun et al. |
| 9,874,531 B2 | 1/2018 | Yun et al. |
| 9,939,392 B2 | 4/2018 | Wen |
| 2001/0006413 A1 | 7/2001 | Burghoorn |
| 2002/0085676 A1 | 7/2002 | Snyder |
| 2003/0142790 A1 | 1/2003 | Zhou et al. |
| 2004/0120463 A1 | 6/2004 | Wilson et al. |
| 2004/0140432 A1 | 7/2004 | Maldonado et al. |
| 2005/0074094 A1 | 4/2005 | Jen et al. |
| 2005/0123097 A1 | 6/2005 | Wang |
| 2005/0163284 A1 | 7/2005 | Inazuru |
| 2005/0282300 A1 | 12/2005 | Yun et al. |
| 2006/0045234 A1 | 3/2006 | Pelc |
| 2006/0062350 A1 | 3/2006 | Yokhin |
| 2007/0030959 A1 | 2/2007 | Ritter |
| 2007/0071174 A1 | 3/2007 | Hebert et al. |
| 2007/0108387 A1 | 5/2007 | Yun et al. |
| 2007/0110217 A1 | 5/2007 | Ukita |
| 2007/0183563 A1 | 8/2007 | Baumann |
| 2007/0183579 A1 | 8/2007 | Baumann et al. |
| 2007/0189449 A1 | 8/2007 | Baumann |
| 2007/0248215 A1 | 10/2007 | Ohshima et al. |
| 2008/0084966 A1 | 4/2008 | Aoki et al. |
| 2008/0089484 A1 | 4/2008 | Reinhold |
| 2008/0094694 A1 | 4/2008 | Yun et al. |
| 2008/0159707 A1 | 7/2008 | Lee et al. |
| 2008/0165355 A1 | 7/2008 | Yasui et al. |
| 2008/0170662 A1 | 7/2008 | Reinhold |
| 2008/0170668 A1 | 7/2008 | Kruit et al. |
| 2008/0181363 A1 | 7/2008 | Fenter et al. |
| 2008/0240344 A1 | 10/2008 | Reinhold |
| 2008/0273662 A1 | 11/2008 | Yun |
| 2009/0052619 A1 | 2/2009 | Endoh |
| 2009/0092227 A1 | 4/2009 | David |
| 2009/0154640 A1 | 6/2009 | Baumann et al. |
| 2009/0316860 A1 | 12/2009 | Okunuki et al. |
| 2010/0012845 A1 | 1/2010 | Baeumer et al. |
| 2010/0027739 A1 | 2/2010 | Lantz et al. |
| 2010/0040202 A1 | 2/2010 | Lee |
| 2010/0061508 A1 | 3/2010 | Takahashi |
| 2010/0091947 A1 | 4/2010 | Niu |
| 2010/0141151 A1 | 6/2010 | Reinhold |
| 2010/0246765 A1 | 9/2010 | Murakoshi |
| 2010/0260315 A1 | 10/2010 | Sato et al. |
| 2010/0272239 A1 | 10/2010 | Lantz et al. |
| 2010/0284513 A1 | 11/2010 | Kawabe |
| 2011/0026680 A1 | 2/2011 | Sato |
| 2011/0038455 A1 | 2/2011 | Silver et al. |
| 2011/0058655 A1 | 3/2011 | Okumura et al. |
| 2011/0064191 A1 | 3/2011 | Toth et al. |
| 2011/0085644 A1 | 4/2011 | Verman |
| 2011/0135066 A1 | 6/2011 | Behling |
| 2011/0142204 A1 | 6/2011 | Zou et al. |
| 2011/0235781 A1 | 9/2011 | Aoki et al. |
| 2011/0243302 A1 | 10/2011 | Murakoshi |
| 2011/0268252 A1 | 11/2011 | Ozawa et al. |
| 2012/0041679 A1 | 2/2012 | Stampanoni |
| 2012/0057669 A1 | 3/2012 | Vogtmeier et al. |
| 2012/0163547 A1 | 6/2012 | Lee et al. |
| 2012/0163554 A1 | 6/2012 | Tada |
| 2012/0224670 A1 | 9/2012 | Kiyohara et al. |
| 2012/0228475 A1 | 9/2012 | Pang et al. |
| 2012/0269323 A1 | 10/2012 | Adler et al. |
| 2012/0269324 A1 | 10/2012 | Adler |
| 2012/0269325 A1 | 10/2012 | Adler et al. |
| 2012/0269326 A1 | 10/2012 | Adler et al. |
| 2012/0294420 A1 | 11/2012 | Nagai |
| 2013/0011040 A1 | 1/2013 | Kido et al. |
| 2013/0032727 A1 | 2/2013 | Kondoe |
| 2013/0039460 A1 | 2/2013 | Levy |

(56) References Cited

U.S. PATENT DOCUMENTS

| | | |
|---|---|---|
| 2013/0108012 A1 | 5/2013 | Sato |
| 2013/0108022 A1 | 5/2013 | Kugland et al. |
| 2013/0195246 A1 | 8/2013 | Tamura et al. |
| 2013/0223594 A1 | 8/2013 | Sprong et al. |
| 2013/0259207 A1 | 10/2013 | Omote et al. |
| 2013/0279651 A1 | 10/2013 | Yokoyama |
| 2013/0308112 A1 | 11/2013 | Clube et al. |
| 2013/0308754 A1 | 11/2013 | Yamazaki et al. |
| 2014/0023973 A1 | 1/2014 | Marconi et al. |
| 2014/0037052 A1 | 2/2014 | Adler |
| 2014/0064445 A1 | 3/2014 | Adler |
| 2014/0072104 A1 | 3/2014 | Jacobsen et al. |
| 2014/0079188 A1 | 3/2014 | Hesselink et al. |
| 2014/0105363 A1 | 4/2014 | Chen et al. |
| 2014/0146945 A1 | 5/2014 | Fredenberg et al. |
| 2014/0153692 A1 | 6/2014 | Larkin et al. |
| 2014/0177800 A1 | 6/2014 | Sato et al. |
| 2014/0185778 A1 | 7/2014 | Lee et al. |
| 2014/0205057 A1 | 7/2014 | Koehler et al. |
| 2014/0211919 A1 | 7/2014 | Ogura et al. |
| 2014/0226785 A1 | 8/2014 | Stutman et al. |
| 2014/0241493 A1 | 8/2014 | Yokoyama |
| 2014/0270060 A1 | 9/2014 | Date et al. |
| 2014/0369469 A1 | 12/2014 | Ogura et al. |
| 2015/0030126 A1 | 1/2015 | Radicke |
| 2015/0030127 A1 | 1/2015 | Aoki et al. |
| 2015/0043713 A1 | 2/2015 | Chen |
| 2015/0049860 A1 | 2/2015 | Das |
| 2015/0055743 A1 | 2/2015 | Vedantham et al. |
| 2015/0055745 A1 | 2/2015 | Holzner et al. |
| 2015/0092924 A1 | 4/2015 | Yun et al. |
| 2015/0110252 A1 | 4/2015 | Yun et al. |
| 2015/0117599 A1 | 4/2015 | Yun et al. |
| 2015/0194287 A1 | 7/2015 | Yun et al. |
| 2015/0243397 A1 | 8/2015 | Yun et al. |
| 2015/0247811 A1 | 9/2015 | Yun et al. |
| 2015/0260663 A1 | 9/2015 | Yun et al. |
| 2015/0357069 A1 | 12/2015 | Yun et al. |
| 2016/0064175 A1 | 3/2016 | Yun et al. |
| 2016/0066870 A1 | 3/2016 | Yun et al. |
| 2016/0106387 A1* | 4/2016 | Kahn ............... A61B 6/5211 378/62 |
| 2016/0351370 A1 | 5/2016 | Yun et al. |
| 2016/0178540 A1 | 6/2016 | Yun et al. |
| 2016/0268094 A1 | 9/2016 | Yun et al. |
| 2016/0320320 A1 | 11/2016 | Yun et al. |
| 2017/0047191 A1 | 2/2017 | Yun et al. |
| 2017/0052128 A1 | 2/2017 | Yun et al. |
| 2017/0162288 A1 | 6/2017 | Yun et al. |
| 2017/0162359 A1 | 6/2017 | Tang et al. |
| 2017/0227476 A1 | 8/2017 | Zhang et al. |
| 2017/0234811 A1 | 8/2017 | Zhang et al. |
| 2017/0261442 A1 | 9/2017 | Yun et al. |
| 2017/0336334 A1 | 11/2017 | Yun et al. |
| 2018/0144901 A1 | 5/2018 | Yun et al. |
| 2018/0261352 A1 | 9/2018 | Matsuyama et al. |

FOREIGN PATENT DOCUMENTS

| | | |
|---|---|---|
| EP | 0751533 | 1/1997 |
| EP | 1028451 | 8/2000 |
| FR | 2548447 | 1/1985 |
| JP | H06-188092 | 7/1994 |
| JP | H07-056000 | 3/1995 |
| JP | 2000-306533 | 11/2000 |
| JP | 2007-265981 | 10/2007 |
| JP | 2007-311185 | 11/2007 |
| JP | 2008-200359 | 4/2008 |
| JP | 2008-197495 | 8/2008 |
| JP | 2009-195349 | 3/2009 |
| JP | 2009-212058 | 9/2009 |
| JP | 2010-236986 | 10/2010 |
| JP | 2011-029072 | 2/2011 |
| JP | 2011-218147 | 11/2011 |
| JP | 2012-187341 | 10/2012 |
| JP | 2013-157269 | 8/2013 |
| JP | 2013-160637 | 8/2013 |
| JP | 2013-239317 | 11/2013 |
| JP | 2015-002074 | 1/2015 |
| JP | 2015-047306 | 3/2015 |
| JP | 2015-077289 | 4/2015 |
| WO | WO 1995/006952 | 3/1995 |
| WO | WO 1998/011592 | 3/1998 |
| WO | WO 2002/039792 | 5/2002 |
| WO | WO 2003/081631 | 10/2003 |
| WO | WO 2005/109969 | 11/2005 |
| WO | WO 2006/096052 | 9/2006 |
| WO | WO 2007/125833 | 11/2007 |
| WO | WO 2009/098027 | 8/2009 |
| WO | WO 2009/1104560 | 8/2009 |
| WO | WO 2011/032572 | 3/2011 |
| WO | WO 2012/032950 | 3/2012 |
| WO | WO 2013/004574 | 1/2013 |
| WO | WO 2013/111050 | 8/2013 |
| WO | WO 2013/118593 | 8/2013 |
| WO | WO 2013/160153 | 10/2013 |
| WO | WO 2013/168468 | 11/2013 |
| WO | WO 2014/054497 | 4/2014 |
| WO | WO 2015/016019 | 2/2015 |
| WO | WO 2015/034791 | 3/2015 |
| WO | WO 2015/066333 | 5/2015 |
| WO | WO 2015/084466 | 6/2015 |
| WO | WO 2015/168473 | 11/2015 |
| WO | WO 2015/176023 | 11/2015 |
| WO | WO 2015/187219 | 12/2015 |
| WO | WO 2016/187623 | 11/2016 |
| WO | WO 2017/204850 | 11/2017 |
| WO | WO 2017/213996 | 12/2017 |

OTHER PUBLICATIONS

"Diamond," Section 10.4.2 of Zorman et al., "Material Aspects of Micro-Nanoelectromechanical Systems," Chapter 10 of Springer Handbook of Nanotechnology, 2nd ed., Barat Bushan, ed. (Springer Science + Business Media, Inc., New York, 2007), pp. 312-314.

"Element Six CVD Diamond Handbook" (Element Six, Luxembourg, 2015).

"High performance benchtop EDXRF spectrometer with Windows® software," published by: Rigaku Corp., Tokyo, Japan; 2017.

"Monochromatic Doubly Curved Crystal Optics," published by: X-Ray Optical Systems, Inc. (XOS), East Greenbush, NY; 2017.

"Optics and Detectors," Section 4 of XS-Ray Data Booklet, 3rd Ed., A.C. Thompson ed. (Lawrence Berkeley Nat'l Lab, Berkeley, CA, 2009).

"Properties of Solids," Ch. 12 of CRC Handbook of Chemistry and Physics, 90th ed., Devid R. Lide & W.M. "Mickey" Haynes, eds. (CRC Press, Boca Raton, FL, 2009), pp. 12-41-12-46; 12-203-12-212.

"Science and Technology of Future Light Sources", Arthur L. Robinson (LBNL) and Brad Plummer (SLAG), eds. Report Nos. ANL-08/39/BNL-81895-2008/LBNL-1090E-2009/SLAC-R-917 (Lawrence Berkeley Nat'l Lab, Berkeley, CA, Dec. 2008).

"Toward Control of Matter: Energy Science Needs for a New Class of X-Ray Light Sources" (Lawrence Berkeley Nat'l Lab, Berkeley, CA, Sep. 2008).

"X-ray Optics for BES Light Source Facilities," Report of the Basic Energy Sciences Workshop on X-ray Optics for BES Light Source Facilities, D. Mills & H. Padmore, Co-Chairs, (U.S. Dept. of Energy, Office of Science, Potomac, MD, Mar. 2013).

Abullian et al., "Quantitative determination of the lateral density and intermolecular correlation between proteins anchored on the membrane surfaces using grazing incidence small-angle X-ray scattering and grazing incidence X-ray fluorescence," Nov. 28, 2012, The Journal of Chemical Physics, vol. 137, pp. 204907-1 to 204907-8.

Adachi et al., "Development of the 17-inch Direct-Conversion Dynamic Flat-panel X-ray Detector (FPD)," Digital R/F (Shimadzu Corp., 2 pages (no date, published-2004 with product release).

(56) References Cited

OTHER PUBLICATIONS

Aharonovich et al., "Diamond Nanophotonics," Adv. Op. Mat'ls vol. 2, Issue 10 (2014).
Als-Nielsen et al., "Phase contrast imaging" Sect. 9.3 of Ch. 9 of "Elements of Modern X-ray Physics, Second Edition", (John Wiley & Sons Ltd, Chichester, West Sussex, UK, 2011), pp. 318-329.
Als-Nielsen et al., "Photoelectric Absorption," Ch. 7 of "Elements of Modern X-ray Physics, Second Edition," (John Wiley & Sons Ltd, Chichester, West Sussex, UK, 2011).
Als-Nielsen et al., "Refraction and reflection from interfaces," Ch. 3 of "Elements of Modern X-ray Physics, Second Edition," (John Wiley & Sons Ltd., Chichester, West Sussex, UK, 2011), pp. 69-112.
Als-Nielsen et al., "X-rays and their interaction with matter", and "Sources", Ch. 1 & 2 of "Elements of Modern X-ray Physics, Second Edition" (John Wiley & Sons Ltd, Chichester, West Sussex, UK, 2011).
Altapova et al., "Phase contrast laminography based on Talbot interferometry," Opt. Express, vol. 20, No. 6, (2012) pp. 6496-6508.
Ando et al., "Smooth and high-rate reactive ion etching of diamond," Diamond and Related Materials, vol. 11, (2002) pp. 824-827.
Arfelli et al., "Mammography with Synchrotron Radiation: Phase-Detection Techniques," Radiology vol. 215, (2000), pp. 286-293.
Arndt et al., Focusing Mirrors for Use with Microfocus X-ray Tubes, 1998, Journal of Applied Crystallography, vol. 31, pp. 733-741.
Balaic et al., "X-ray optics of tapered capillaries," Appl. Opt. vol. 34 (Nov. 1995) pp. 7263-7272.
Baltes et al., "Coherent and incoherent grating reconstruction," J. Opt. Soc. Am. A vol. 3(8), (1986), pp. 1268-1275.
Barbee Jr., "Multilayers for x-ray optics," Opt. Eng. vol. 25 (Aug. 1986) pp. 898-915.
Baron et al., "A compact optical design for Bragg reflections near backscattering," J. Synchrotron Rad., vol. 8 (2001), pp. 1127-1130.
Bech, "In-vivo dark-field and phase-contrast x-ray imaging," Scientific Reports 3, (2013), Article number: 03209.
Bech, "X-ray imaging with a grating interferometer," University of Copenhagen PhD. Thesis, (May 1, 2009).
Bergamin et al., "Measuring small lattice distortions in Si-crystals by phase-contrast x-ray topography," J. Phys. D: Appl. Phys. vol. 33 (Dec. 31, 2000) pp. 2678-2682.
Bernstorff, "Grazing Incidence Small Angle X-ray Scattering (GISAXS)," Presentation at Advanced School on Synchrotron and Free Electron Laser Sources and their Multidisciplinary Applications, Apr. 2008, Trieste, Italy.
Bilderback et al., "Single Capillaries," Ch. 29 of "Handbook of Optics vol. III, 2nd Ed." (McGraw Hill, New York, 2001).
Birkholz, "Chapter 4: Grazing Incidence Configurations," Thin Film Analysis by X-ray Scattering (Wiley-VCH Verlag GmbH & Co. KGaA, Weinheim, Germany, 2006).
Bjeoumikhov et al., "A modular system for XRF and XRD applications consisting of a microfocus X-ray source and different capillary optics," X-ray Spectrometry, vol. 33 (2004), pp. 312-316.
Bjeoumikhov et al., "Capillary Optics for X-Rays," Ch. 18 of "Modern Developments in X-Ray and Neutron Optics," A. Erko et al., eds. (Springer, Berlin, Germany, 2008), pp. 287-306.
Canberra Model S-5005 WinAxil X-Ray Analysis Software, published by: Canberra Eurisys Benelux N.V./S.A., Zellik, Belgium, Jun. 2004.
Cerrina, "The Schwarzschild Objective," Ch. 27 of "Handbook of Optics vol. III, 2nd Ed." (McGraw Hill, New York, 2001).
Chen et al., "Advance in detection of low sulfur content by wavelength dispersive XRF," Proceedings of the Annual ISA Analysis Division Symposium (2002).
Chen et al., "Doubly curved crystal (DCC) X-ray optics and applications," Powder Diffraction, vol. 17(2) (2002), pp. 99-103.
Chen et al., "Guiding and focusing neutron beams using capillary optics," Nature vol. 357 (Jun. 4, 1992), pp. 391-393.

Chervenak et al., "Experimental thick-target bremsstrahlung spectra from electrons in the range 10 to 30 keV", Phys. Rev. A vol. 12 (1975), pp. 26-33.
Coan et al., "In vivo x-ray phase contrast analyzer-based imaging for longitudinal osteoarthritis studies in guinea pigs," Phys. Med. Biol. vol. 55(24) (2010), pp. 7649-7662.
Cockcroft et al., "Chapter 2: Experimental Setups," Powder Diffraction: Theory and Practice, R.E. Dinnebier and S.J.L. Billinge, eds (Royal Society of Chemistry Publishing, London, UK, 2008).
Cohen et al., "Tunable laboratory extended x-ray absorption fine structure system," Rev. Sci. Instr. vol. 51, No. 3, Mar. 1980, pp. 273-277.
Cong et al., "Fourier transform-based iterative method for differential phase-contrast computed tomography", Opt. Lett. vol. 37 (2012), pp. 1784-1786.
Cornaby et al., "Advances in X-ray Microfocusing with Monocapillary Optics at CHESS," CHESS News Magazine (2009), pp. 63-66.
Cornaby et al., "Design of Single-Bounce Monocapillary X-ray Optics," Advances in X-ray Analysis: Proceedings of the 55th Annual Conference on Applications of X-ray Analysis, vol. 50, (International Centre for Diffraction Data (ICDD), 2007), pp. 194-200.
Cornaby, "The Handbook of X-ray Single Bounce Monocapillary Optics, Including Optical Design and Synchrotron Applications" (PhD Dissertation, Cornell University, Ithaca, NY, May 2008).
David et al., "Fabrication of diffraction gratings for hard x-ray phase contrast imaging," Microelectron. Eng. vol. 84, (2007), pp. 1172-1177.
David et al., "Hard X-ray phase imaging and tomography using a grating interferometer," Spectrochimica Acta Part B vol. 62 (2007) pp. 626-630.
Davis et al., "Bridging the Micro-to-Macro Gap: A New Application for Micro X-Ray Fluorescence," Microsc Microanal., vol. 17(3) (Jun. 2011), pp. 410-417.
Diaz et al., "Monte Carlo Simulation of Scatter Field for Calculation of Contrast of Discs in Synthetic CDMAM Images," In: Digital Mammography, Proceedings 10th International Workshop IWDM 2010 (Springer Verlag, Berlin Heidelberg), (2010), pp. 628-635 (9 pages). Jun. 18, 2010.
Ding et al., "Reactive Ion Etching of CVD Diamond Films for MEMS Applications," Micromachining and Microfabrication, Proc. SPIE vol. 4230 (2000), pp. 224-230.
Dobrovinskaya et al., "Thermal Properties," Sect. 2.1.5 of "Sapphire: Material, Manufacturing, Applications" (Springer Science + Business Media, New York, 2009).
Erko et al., "X-ray Optics," Ch. 3 of "Handbook of Practical X-Ray Fluorescence Analysis," B. Beckhoff et al., eds. (Springer, Berlin, Germany, 2006), pp. 85-198.
Falcone et al., "New directions in X-ray microscopy," Contemporary Physics, vol. 52, No. 4, (Jul.-Aug. 2010), pp. 293-318.
Fernández-Ruiz, "TXRF Spectrometry as a Powerful Tool for the Study of Metallic Traces in Biological Systems," Development in Analytical Chemistry, vol. 1 (2014), pp. 1-14.
Freund, "Mirrors for Synchrotron Beamlines," Ch. 26 of "Handbook of Optics vol. III, 2nd Ed." (McGraw Hill, New York, 2001).
Ge et al., "Investigation of the partially coherent effects in a 2D Talbot interferometer," Anal. Bioanal. Chem. vol. 401, (2011), pp. 865-870. Apr. 29, 2011 pub Jun. 14, 2011.
Gibson et al., "Polycapillary Optics: An Enabling Technology for New Applications," Advances in X-ray Analysis, vol. 45 (2002), pp. 286-297.
Gonzales et al., "Angular Distribution of Bremsstrahlung Produced by 10-Kev and 20 Kev Electrons Incident on a Thick Au Target", in Application of Accelerators in Research and Industry, AIP Conf. Proc. 1221 (2013), pp. 114-117.
Gonzales et al., "Angular distribution of thick-target bremsstrahlung produced by electrons with initial energies ranging from 10 to 20 keV incident on Ag", Phys. Rev. A vol. 84 (2011): 052726.
Guttmann et al., "Ellipsoidal capillary as condenser for the BESSSY full-field x-ray microscope," J. Phys. Conf. Ser. vol. 186 (2009): 012064.

(56) References Cited

OTHER PUBLICATIONS

Harasse et al., "Iterative reconstruction in x-ray computed laminography from differential phase measurements", Opt. Express. vol. 19 (2011), pp. 16560-16573.
Harasse et al., "X-ray Phase Laminography with a Grating Interferometer using Iterative Reconstruction", in International Workshop on X-ray and Neutron Phase Imaging with Gratings, AIP Conf. Proc. vol. 1466, (2012), pp. 163-168.
Harasse et al., "X-ray Phase Laminography with Talbot Interferometer", in Developments in X-Ray Tomography VII, Proc. Spie vol. 7804 (2010), 780411.
Hasse et al., "New developments in laboratory-based x-ray sources and optics," Adv. In Laboratory-based X-Ray Sources, Optics, and Applications VI, ed. A.M. Khounsary, Proc. SPIE vol. 10387, 103870B-1 (2017).
Hemraj-Benny et al., "Near-Edge X-ray Absorption Fine Structure Spectroscopy as a Tool for Investigating Nanomaterials," Small, vol. 2(1), (2006), pp. 26-35.
Henke et al., "X-ray interactions: photoabsorption, scattering, transmission, and reflection at E=50-30000 eV, Z=1-92," Atomic Data and Nuclear Data Tables, vol. 54 (No. 2) (Jul. 1993), pp. 181-342.
Honma et al., Full-automatic XAFS Measurement System of the Engineering Science Research II beamline BL14B2 at Spring-8, 2011, AIP Conference Proceedings 1234, pp. 13-16.
Howard et al., "High-Definition X-ray Fluorescence Elemental Mapping of Paintings," Anal. Chem., 2012, vol. 84(7), pp. 3278-3286.
Howells, "Gratings and Monochromators in the VUV and Soft X-RAY Spectral Region," Ch. 21 of Handbook of Optics vol. III, 2nd Ed. (McGraw Hill, New York, 2001).
Howells, "Mirrors for Synchrotron-Radiation Beamlines," Publication LBL-34750 (Lawrence Berkeley Laboratory, Berkeley, CA, Sep. 1993).
Hrdý et al, "Diffractive-Refractive Optics: X-ray Crystal Monochromators with Profiled Diffracting Surfaces," Ch. 20 of "Modern Developments in X-Ray and Neutron Optics," A. Erko et al., eds. (Springer, Berlin Heidelberg New York, 2008).
Hwang et al, "New etching process for device fabrication using diamond," Diamond & Related Materials, vol. 13 (2004) pp. 2207-2210.
Ide-Ektessabi et al., "The role of trace metallic elements in neurodegenerative disorders: quantitative analysis using XRF and XANES spectroscopy," Anal. Sci., vol. 21(7) (Jul. 2005), pp. 885-892.
Ihsan et al., "A microfocus X-ray tube based on a microstructured X-ray target", Nuclear Instruments and Methods in Physics Research B vol. 267 (2009) pp. 3566-3573.
Ishisaka et al., "A New Method of Analyzing Edge Effect in Phase Contrast Imaging with Incoherent X-rays," Optical Review, vol. 7, No. 6, (2000), pp. 566-572.
Ito et al., "A Stable In-Laboratory EXAFS Measurement System," Jap. J. Appl. Phys., vol. 22, No. 2, Feb. 1, 1983, pp. 357-360.
Itoh et al., "Two-dimensional grating-based X-ray phase-contrast imaging using Fourier transform phase retrieval," Op. Express, vol. 19, No. 4 (2011) pp. 3339-3346.
Janssens et al, "Recent trends in quantitative aspects of microscopic X-ray fluorescence analysis," TrAC Trends in Analytical Chemistry 29.6 (Jun. 2010): 464-478.
Jiang et al., "X-Ray Phase-Contrast Imaging with Three 2D Gratings," Int. J. Biomed. Imaging, (2008), 827152, 8 pages.
Joy, "Astronomical X-ray Optics," Ch. 28 of "Handbook of Optics vol. III, 2nd Ed.," (McGraw Hill, New York, 2001).
Keyrilainen et al., "Phase contrast X-ray imaging of breast," Acta Radiologica, vol. 51 (8), (2010), pp. 866-884. Jan. 18, 2010 pub Jun. 6, 2010.
Kidalov et al., "Thermal Conductivity of Diamond Composites," Materials, vol. 2 (2009) pp. 2467-2495.
Kido et al., "Bone Cartilage Imaging with X-ray Interferometry using a Practical X-ray Tube", in Medical Imaging 2010: Physics of Medical Imaging, Proc. SPIE vol. 7622 (2010), 762240.
Kim, "Talbot images of wavelength-scale amplitude gratings," Opt. Express vol. 20(5), (2012), pp. 4904-4920.
Kirkpatrick et al., "Formation of Optical Images by X-Rays", J. Opt. Soc. Am. vol. 38(9) (1948), pp. 766-774.
Kirz, "Phase zone plates for x rays and the extreme uv," J. Op. Soc. Am. vol. 64 (Mar. 1974), pp. 301-309.
Kirz et al., "The History and Future of X-ray Microscopy", J. Physics: Conden. Series vol. 186 (2009): 012001.
Kiyohara et al., "Development of the Talbot-Lau Interferometry System Available for Clinical Use", in International Workshop on X-ray and Neutron Phase Imaging with Gratings, AIP Cong. Proc. vol. 1466, (2012), pp. 97-102.
Klockenkämper et al., "7.1 Instrumental Developments" and "7.3 Future Prospects by Combinations," from Chapter 7 of Total Reflection X-ray Fluorescence Analysis and Related Methods 2nd Ed. (J. Wiley and Sons, Hoboken, NJ, 2015).
Klockenkämper et al., "Chapter 3: Instrumentation for TXRF and GI-XRF," Total Reflection X-ray Fluorescence Analysis and Related Methods 2nd Ed. (J. Wiley and Sons, Hoboken, NJ, 2015).
Kottler et al., "A two-directional approach for grating based differential phase contrast imaging using hard x-rays," Opt. Express vol. 15(3), (2007), pp. 1175-1181.
Kottler et al., "Dual energy phase contrast x-ray imaging with Talbot-Lau interferometer," J. Appl. Phys. vol. 108(11), (2010), 114906. Jul. 7, 2010 pub Dec. 7, 2010.
Kumakhov et al., "Multiple reflection from surface X-ray optics," Physics Reports, vol. 191(5), (1990), pp. 289-350.
Kumakhov, "X-ray Capillary Optics. History of Development and Present Status" in Kumakhov Optics and Application, Proc. SPIE 4155 (2000), pp. 2-12.
Kuwabara et al., "Hard-X-ray Phase-Difference Microscopy with a Low-Brilliance Laboratory X-ray Source", Appl. Phys. Express vol. 4 (2011) 062502.
Kuznetsov, "X-Ray Optics Calculator," Institute of Microelectronics Technology and High Purity Materials, Russian Academy of Sciences (IMT RAS), Chernogolovka, Russia (6 pages submitted); 2016.
Lagomarsino et al., "Reflective Optical Arrays," Ch. 19 of "Modern Developments in X-Ray and Neutron Optics," A. Erko et al. eds. (Springer, Berlin, Germany, 2008), pp. 307-317.
Lai, "X-Ray Microfocusing Optics," Slide Presentation from Argonne National Laboratory, 71 slides, Cheiron Summer School 2007.
Langhoff et al., "X-ray Sources," Ch. 2 of "Handbook of Practical X-Ray Fluorescence Analysis," B. Beckhoff et al., eds. (Springer, Berlin Heidelberg New York, 2006), pp. 33-82.
Lechner et al., "Silicon drift detecors for high count rate X-ray spectroscopy at room temperature," Nuclear Instruments and Methods, vol. 458A (2001), pp. 281-287.
Leenaers et al., "Application of Glancing Incidence X-ray Analysis," 1997, X-ray Spectrometry, vol. 26, pp. 115-121.
Lengeler et al., "Refractive X-ray Optics," Ch. 20 of "Handbook of Optics vol. III, 2nd Ed." (McGraw Hill, New York, 2001.
Li et al., "Source-optic-crystal optimisation for compact monochromatic imaging," Proc. SPIE 5537 (2004), pp. 105-114.
Lohmann et al., "An interferometer based on the Talbot effect," Optics Communications vol. 2 (1971), pp. 413-415.
Macdonald et al., "An Introduction to X-ray and Neutron Optics," Ch. 19 of "Handbook of Optics vol. III, 2nd Ed." (McGraw Hill, New York, 2001).
Macdonald et al., "Polycapillary and Multichannel Plate X-Ray Optics," Ch. 30 of "Handbook of Optics vol. III, 2nd Ed.," (McGraw Hill, New York, 2001).
Macdonald et al., "Polycapillary X-ray Optics for Microdiffraction," J. Appl. Cryst., vol. 32 (1999) pp. 160-167.
Macdonald, "Focusing Polycapillary Optics and Their Applications," X-Ray Optics and Instrumentation, vol. 2010, (Oct. 2010): 867049.
Maj et al., "Etching methods for improving surface imperfections of diamonds used for x-ray monochromators," Adv. X-ray Anal., vol. 48 (2005), pp. 176-182.
Malgrange, "X-ray Optics for Synchrotron Radiation," ACTA Physica Polinica A, vol. 82(1) (1992) pp. 13-32.

(56) References Cited

OTHER PUBLICATIONS

Masuda et al., "Fabrication of Through-Hole Diamond Membranes by Plasma Etching Using Anodic Porous Alumina Mask," Electrochemical and Solid-State Letters, vol. 4(11) (2001) pp. G101-G103.
Matsushita, "Mirrors and Multilayers," Slide Presentation from Photon Factory, Tsukuba, Japan, 65 slides, (Cheiron School 2009, Sprint-8, Japan, Nov. 2009).
Matsushita, "X-ray monochromators," Slide Presentation from Photon Factory, Tsukuba, Japan, 70 slides, (Cheiron School 2009, Spring-8, Japan, Nov. 2009).
Matsuyama et al., "Wavefront measurement for a hard-X-ray nanobeam using single-grating interferometry", Opt Express vol. 20 (2012), pp. 24977-24986.
Miao et al., "Motionless phase stepping in X-ray phase contrast imaging with a compact source," Proceedings of the National Academy of Sciences, vol. 110(48), (2013), pp. 19268-19272.
Michette, "Zone and Phase Plates, Bragg-Fresnel Optics," Ch. 23 of "Handbook of Optics vol. III, 2nd Ed.," (McGraw Hill, New York, 2001).
Mizutani et al., X-ray microscopy for neural circuit reconstruction in 9th International Conference on X-Ray Microscopy, J. Phys: Conf. Ser. 186 (2009) 012092.
Modregger et al., "Grating-Based X-ray Phase Contrast Imaging," Ch. 3 of Emerging Imaging Technologies in Medicine, M. Anastasio & P. La Riviere, ed., CRC Press, Boca Raton, FL, (2012), pp. 43-56.
Momose et al., "Biomedical Imaging by Talbot-Type X-Ray Phase Tomography" in Developments in X-Ray Tomography V, Proc. SPIE vol. 6318 (2006) 63180T.
Momose et al., "Grating-Based X-ray Phase Imaging Using Multiline X-ray Source", Jpn. J. Appl. Phys. vol. 48 (2009), 076512.
Momose et al., "Phase Tomography by X-ray Talbot Interferometry for Biological Imaging" Jpn. J. Appl. Phys. vol. 45 2006 pp. 5254-5262.
Momose et al., "Phase Tomography Using X-ray Talbot Interferometer", in Synchrotron Radiation Instrumentation: Ninth International Conference, AIP Conf. Proc. vol. 879 (2007), pp. 1365-1368.
Momose et al., "Phase-Contrast X-Ray Imaging Using an X-Ray Interferometer for Biological Imaging", Analytical Sciences vol. 17 Supplement (2001), pp. i527-i530.
Momose et al., "Sensitivity of X-ray Phase Imaging Based on Talbot Interferometry", Jpn. J. Appl. Phys. vol. 47 (2008), pp. 8077-8080.
Momose et al., "X-ray Phase Measurements with Talbot Interferometry and Its Applications", in International Conference on Advanced Phase Measurement Methods in Optics and Imaging, AIP Conf. Proc. vol. 1236 (2010), pp. 195-199.
Momose et al., "X-ray Phase Imaging—From Static Observation to Dynamic Observation—", in International Workshop on X-ray and Neutron Phase Imaging with Gratings AIP Conf. Proc. vol. 1466, (2012), pp. 67-77.
Momose et al., "X-ray Phase Imaging Using Lau Effect", Appl. Phys. Express vol. 4 (2011) 066603.
Momose et al., "X-Ray Phase Imaging with Talbot Interferometry", in "Biomedical Mathematics: Promising Directions in Imaging, Therapy Planning, and Inverse Problems", Y. Censor, M. Jiang & G. Wang, eds. (Medical Physics Publishing, Madison, WI, USA, 2010), pp. 281-320.
Momose et al., "X-ray phase tomography with a Talbot interferometer in combination with an X-ray imaging microscope", in 9th International Conference on X-Ray Microscopy, J. Phys: Conf. Ser. 186 (2009) 012044.
Momose et al., "X-ray Talbot Interferometry with Capillary Plates", Jpn. J. Appl. Phys. vol. 45 (2006), pp. 314-316.
Momose et al., "Four-dimensional X-ray phase tomography with Talbot interferometry and white synchrotron radiation: dynamic observation of a living worm", Opt. Express vol. 19 (2011), pp. 8423-8432.
Momose et al., "High-speed X-ray phase imaging and X-ray phase tomography with Talbot interferometer and white synchrotron radiation", Opt. Express vol. 17 (2009), pp. 12540-12545.
Momose et al., "Phase Imaging with an X-ray Talbot Interferometer", Advances in X-ray Analysis vol. 49(3) (2006), pp. 21-30.
Momose et al., "Demonstration of X-Ray Talbot Interferometry", Jpn. J. Appl. Phys. vol. 42 (2003), pp. L866-L868.
Momose et al., "Phase Tomography Using an X-ray Talbot Interferometer", in Developments in X-Ray Tomography IV, Proc. SPIE vol. 5535 (2004), pp. 352-360.
Momose, "Recent Advances in X-ray Phase Imaging", Jpn. J. Appl. Phys. vol. 44 (2005), pp. 6355-6367.
Montgomery, "Self Imaging Objects of Infinite Aperture," J. Opt. Soc. Am. vol. 57(6), (1967), pp. 772-778.
Morimoto et al., "Development of multiline embedded X-ray targets for X-ray phase contrast imaging," XTOP 2012 Book of Abstracts, (Ioffe Physical-Technical Institute of the Russian Academy of Sciences, St. Petersburg, Russia, 2012), pp. 74-75.
Morimoto et al., X-ray phase contrast imaging by compact Talbot-Lau interferometer with a signal transmission grating, 2014, Optics Letters, vol. 39, No. 15, pp. 4297-4300.
Munro et al., Design of a novel phase contrast imaging system for mammography, 2010, Physics in Medicine and Biology, vol. 55, No. 14, pp. 4169-4185.
Nango et al., "Talbot-defocus multiscan tomography using the synchrotron X-ray microscope to study the lacuno-canalicular network in mouse bone", Biomed. Opt. Express vol. 4 (2013), pp. 917-923.
Neuhausler et al., "Non-destructive high-resolution X-ray imaging of ULSI micro-electronics using keV X-ray microscopy in Zernike phase contrast," Microelectronic Engineering, Elsevier Publishers BV., Amsterdam, NO, vol. 83, No. 4-9 (Jan. 4, 2006) pp. 1043-1046.
Newville, "Fundamentals of XAFS," (Univ. of Chicago, Chicago, IL, Jul. 23, 2004).
Noda et al., "Fabrication of Diffraction Grating with High Aspect Ratio Using X-ray Lithography Technique for X-ray Phase Imaging," Jpn. J. Appl. Phys. vol. 46, (2007), pp. 849-851.
Noda et al., "Fabrication of High Aspect Ratio X-ray Grating Using X-ray Lithography" J. Solid Mech_ Mater. Eng. vol. 3 (2009), pp. 416-423.
Nojeh, "Carbon Nanotube Electron Sources: From Electron Beams to Energy Conversion and Optophononics", ISRN Nanomaterials vol. 2014 (2014): 879827.
Nuhn, "From storage rings to free electron lasers for hard x-rays", J.A37 Phys.: Condens. Matter vol. 16 (2004), pp. S3413-S34121.
Nykanen et al., "X-ray scattering in full-field digital mammography," Med. Phys. vol. 30(7), (2003), pp. 1864-1873.
Oji et al., Automatic XAFS measurement system developed at BL14B2 in SPring-8, Available online Nov. 15, 2011, Journal of Synchrotron Radiation, vol. 19, pp. 54-59.
Olbinado et al., "Demonstration of Stroboscopic X-ray Talbot Interferometry Using Polychromatic Synchrotron and Laboratory X-ray Sources", Appl. Phys. Express vol. 6 (2013), 096601.
Ortega et al., "Bio-metals imaging and speciation in cells using proton and synchrotron radiation X-ray microspectroscopy," J. Royal Society Interface vol. 6 suppl. 5 (Oct. 6, 2009), pp. 6S649-6S658.
Otendal et al., A 9 keV electron-impact liquid-gallium-jet x-ray source, Rev. Sci. Instrum. vol. 79 (2008): 016102.
Oxford Instruments Inc., Series 5000 Model XTF5011 X-ray Tube information, Jun. 1998, 3 pages.
Parrill et al., "GISAXS—Glancing Incidence Small Angle X-ray Scattering," Journal de Physique IV, vol. 3 (Dec. 1993), pp. 411-417.
Paxscan Flat Panel X-ray Imaging, Varian Sales Brochure, (Varian Medical Systems, Palo Alto, CA, Nov. 11, 2004).
Pfeiffer et al., " Hard-X-ray dark-field imaging using a grating interferometer," Nature Materials vol. 7, (2008), pp. 134-137.
Pfeiffer et al., "Hard x-ray phase tomography with low brilliance x-ray sources," Phys. Rev. Lett. vol. 98, (2007), 108105.
Pfeiffer et al., "Phase retrieval and differential phase-contrast imaging with low-brilliance X-ray sources," Nature Physics vol. 2, (2006), pp. 258-261.

(56) References Cited

OTHER PUBLICATIONS

Pfeiffer, "Milestones and basic principles of grating-based x-ray and neutron phase-contrast imaging," in International Workshop on X-ray and Neutron Phase Imaging with Gratings AIP Conf. Proc. vol. 1466, (2012), pp. 2-11.
Pianetta et al., "Application of synchrotron radiation to TXRF analysis of metal contamination on silicon wafer surfaces," Thin Solid Films, vol. 373(1-2), 2000, pp. 222-226.
Potts, "Electron Probe Microanalysis", Ch. 10 of "A Handbook of Silicate Rock Analysis" (Springer Science +Business Media, New York, 1987), pp. 326-382 (equation quoted from p. 336).
Prewitt et al., "FIB Repair of 5X Recticles and Effects on IC Quality," Integrated Circuit Metrology, Inspection, and Process Control VII, Proc. SPIE vol. 1926 (1993), pp. 517-526.
Prewitt et al., "Focused ion beam repair: staining of photomasks and reticles," J. Phys. D Appl. Phys. vol. 26 (1993), pp. 1135-1137.
Prewitt et al., "Gallium Staining in FIB Repair of Photomasks," Microelectronic Engineering, vol. 21 (1993), pp. 191-196.
Qin et al., "Trace metal imaging with high spatial resolution: Applications in biomedicine," Metallomics, vol. 3 (Jan. 2011), pp. 28-37.
Rayleigh, "On copying diffraction gratings and some phenomena connected therewith," Philos. Mag. vol. 11 (1881), pp. 196-205.
Renaud et al., "Probing surface and interface morphology with Grazing Incidence Small Angle X-ray Scattering," Surface Science Reports, vol. 64:8 (2009), pp. 255-380.
Riege, "Electron Emission from Ferroelectrics—A Review", CERN Report CERN AT/93-18 (CERN, Geneva, Switzerland, Jul. 1993).
Röntgen, Ueber eine neue Art von Strahlen (Wurzburg Verlag, Warzburg, Germany, 1896) also, in English, "On a New Kind of Rays," Nature vol. 53 (Jan. 23, 1896). pp. 274-276.
Rovezzi, "Study of the local order around magnetic impurities in semiconductors for spintronics." PhD Dissertation, Condensed Matter, UniversitéJoseph-Fourier—Grenoble I, 2009, English <tel-00442852>.
Rutishauser, "X-ray grating interferometry for imaging and metrology," 2003, Eth Zurich, Diss. ETH No. 20939.
Sato et al., Two-dimensional gratings-based phase-contrast imaging using a conventional x-ray tube, 2011, Optics Letters, vol. 36, No. 18, pp. 3551-3553.
Scherer et al., "Bi-Directional X-Ray Phase-Contrast Mammography," PLoS ONE, vol. 9, Issue 5 (May 2014) e93502.
Scholz, "X-ray Tubes and Monochromators," Technical Workshop EPIV, Universität Würzburg (2007); 41 slides, 2007.
Scholze et al., "X-ray Detectors and XRF Detection Channels," Ch. 4 of "Handbook of Practical X-Ray Fluorescence Analysis," B. Beckhoff et al., eds. (Springer, Berlin Heidelberg, Germay, 2006), pp. 85-198.
Sebert, "Flat-panel detectors: how much better are they?" Pediatr. Radiol. vol. 36 (Suppl 2), (2006), pp. 173-181.
Shen, "Polarizing Crystal Optics," Ch. 25 of "Handbook of Optics vol. III, 2nd Ed.," (McGraw Hill, New York, 2001).
Shields et al., "Overview of Polycapillary X-ray Optics," Powder Diffraction, vol. 17(2) (Jun. 2002), pp. 70-80.
Shimura et al., "Hard x-ray phase contrast imaging using a tabletop Talbot-Lau interferometer with multiline embedded x-ray targets", Opt. Lett. vol. 38(2) (2013), pp. 157-159.
Siddons, "Crystal Monochromators and Bent Crystals," Ch. 22 of "Handbook of Optics vol. III, 2nd Ed.," (McGraw Hill, New York, 2001).
Smith, "Fundamentals of Digital Mammography: Physics, Technology and Practical Considerations," Publication R-BI-016 (Hologic, Inc., Bedford, MA, Mar. 2005).
Snigirev et al., "Hard X-Ray Microoptics," Ch. 17 of "Modern Developments in X-Ray and Neutron Optics," A. Erko et al., eds (Springer, Berlin, Germany, 2008), pp. 255-285.
Sparks Jr., "X-ray Fluorescence Microprobe for Chemical Analysis," in Synchrotron Radiation Research, H. Winick & S. Doniach, eds. (Plenum Press, New York, NY 1980), pp. 459-512.

Spiller, "Multilayers," Ch. 24 of "Handbook of Optics vol. III, 2nd Ed.," (McGraw Hill, New York, 2001).
Stampanoni et al., "The First Analysis and Clinical Evaluation of Native Breast Tissue Using Differential Phase-Contrast Mammography," Investigative Radiology, vol. 46, pp. 801-806. pub Dec. 2011-xx.
Strüder et al., "Silicon Drift Detectors for X-ray Imaging," Presentation at Detector Workshop on Synchrotron Radiation Instrumentation, 54 slides, (Argonne Nat'l Lab, Argonne, IL Dec. 8, 2005), available at: <http://www.aps.anl.gov/News/Conferences/2005/Synchrotron_Radiation_Instrumentation/Presentations/Strueder.pdf>.
Strüder et al., "X-Ray Detectors," Ch. 4 of "X-ray Spectrometry: Recent Technological Advances," K. Tsuji et al. eds. (John Wiley & Sons, Ltd. Chichester, West Sussex, UK, 2004), pp. 63-131.
Suzuki et al., "Hard X-ray Imaging Microscopy using X-ray Guide Tube as Beam Condenser for Field Illumination," J. Phys.: Conf. Ser. vol. 463 (2013): 012028.
Suzuki, "Development of the DIGITEX Safire Cardiac System Equipped with Direct conversion Flat Panel Detector," Digital Angio Technical Report (Shimadzu Corp., Kyoto, Japan, no date, published—2004 with product release).
Takahama, "RADspeed safire Digital General Radiography System Equipped with New Direct-Conversion FPD," Medical Now, No. 62 (2007).
Takeda et al., "Differential Phase X-ray Imaging Microscopy with X-ray Talbot Interferometer" Appl. Phys. Express vol. 1 (2008) 117002.
Takeda et al., "X-Ray Phase Imaging with Single Phase Grating", Jpn. J. Appl. Phys. vol. 46 (2007), pp. L89-L91.
Takeda et al., "In vivo physiological saline-infused hepatic vessel imaging using a two-crystal-interferometer-based phase-contrast X-ray technique", J. Synchrotron Radiation vol. 19 (2012), pp. 252-256.
Talbot, "Facts relating to optical science No. IV," Philos. Mag. vol. 9 (1836), pp. 401-407.
Tanaka et al., "Cadaveric and in vivo human joint imaging based on differential phase contrast by X-ray Talbot-Lau interferometry", Z. Med. Phys. vol. 23 (2013), pp. 222-227.
Tang et al., "Micro-computed tomography (Micro-CT): a novel appraoch for intraoperative breast cancer specimen imaging," Breast Cancer Res. Treat. vol. 139, pp. 311-316 (2013).
Taniguchi et al., "Diamond nanoimprint lithography," Nanotechnology, vol. 13 (2002) pp. 592-596.
Tkachuk et al., "High-resolution x-ray tomography using laboratory sources", in Developments in X-Ray Tomography V, Proc. SPIE 6318 (2006): 631810.
Tkachuk et al., "Multi-length scale x-ray tomography using laboratory and synchrotron sources", Microsc. Microanal. vol. 13 (Suppl. 2) (2007), pp. 1570-1571.
Touzelbaev et al., "Applications of micron-scale passive diamond layers for the integrated circuits and microelectromechanical systems industries," Diamond and Rel. Mat'ls, vol. 7 (1998) pp. 1-14.
Tsuji et al., "X-Ray Spectrometry: Recent Technological Acvances," John Wiley & Sons Ltd. Chichester, West Susses, UK 2004), Chapters 1-7.
Udagawa, "An Introduction to In-House EXAFS Facilities," The Rigaku Journal, vol. 6, (1) (1989), pp. 20-27.
Udagawa, "An Introduction to X-ray Absorption Fine Structure," The Rigaku Journal, vol. 11(2)(1994), pp. 30-39.
Uehara et al., "Effectiveness of X-ray grating interferometry for non-destructive inspection of packaged devices", J. Appl. Phys. vol. 114 (2013), 134901.
Vogt, "X-ray Fluorescence Microscopy: A Tool for Biology, Life Science and Nanomedicine," Presentation on May 16, 2012 at James Madison Univ., Harrisonburg, VA (31 slides), 2012.
Wan et al.,"Fabrication of Multiple Slit Using Stacked-Sliced Method for Hard X-ray Talbot—Lau Interferometer", Jpn. J. Appl. Phys. vol. 47 (2008), pp. 7412-7414.
Wang et al., "Advantages of intermediate X-ray energies in Zernicke phase constrast X-ray microscopy," Biotech. Adv., vol. 31 (2013) pp. 387-392.

(56) References Cited

OTHER PUBLICATIONS

Wang et al., "Non-invasive classification of microcalcifications with phase-contrast X-ray mammography," Nature Comm. vol. 5:3797, pp. 1-9 (2014).
Wang, On the single-photon-counting (SPC) modes of imaging using an XFEL source, presented at IWORLD2015.
Wang et al., "Precise patterning of diamond films for MEMS application" Journal of Materials Processing Technology vol. 127 (2002), pp. 230-233.
Weitkamp et al., "Design aspects of X-ray grating interferometry," in International Workshop on X-ray and Neutron Phase Imaging with Gratings AIP Conf. Proc. vol. 1466, (2012), pp. 84-89.
Weitkamp et al., "Hard X-ray phase imaging and tomography with a grating interferometer," Proc. SPIE vol. 5535, (2004), pp. 137-142.
Weitkamp et al., "X-ray wavefront diagnostics with Talbot interferometers," International Workshop on X-Ray Diagnostics and Scientific Application of the European XFEL, Ryn, Poland, (2010), 36 slides.
Weitkamp et al., Tomography with grating interferometers at low-brilliance sources, 2006, SPIE, vol. 6318, pp. 0S-1 to 0S-10.
Weitkamp et al., "X-ray phase imaging with a grating interferometer," Opt. Express vol. 13(16), (2005), pp. 6296-6304.
Weitkamp et al., "X-ray wavefront analysis and optics characterization with a grating interferometer," Appl. Phys. Lett. vol. 86, (2005), 054101.
Wen et al., "Fourier X-ray Scattering Radiography Yields Bone Structural Information," Radiology, vol. 251 (2009) pp. 910-918.
Wen et al., "Single-shot x-ray differential phase-contrast and diffraction imaging using two-dimensional transmission gratings," Op. Lett. vol. 35, No. 12, (2010) pp. 1932-1934.
Wobrauschek et al., "Energy Dispersive, X-Ray Fluorescence Analysis," Encyclopedia of Analytical Chemistry, R.A. Meyers, Ed. (Wiley 2010).
Wobrauschek et al., "Micro XRF of light elements using a polycapillary lens and an ultra-thin window Silicon Drift Detector inside a vacuum chamber," 2005, International Centre for Diffraction Data 2005, Advances in X-ray Analysis, vol. 48, pp. 229-235.
Wolter, "Spiegelsysteme streifenden Einfalls als abbildende Optiken fur Rontgenstrahlen" [Grazing Incidence Reflector Systems as Imaging Optics for X-rays] Annalen der Physik vol. 445, Issue 1-2 (1952), pp. 94-114.
X-ray-Optics.de Website, http://www.x-ray-optics.de/, accessed Feb. 13, 2016.
Yakimchuk et al., "Ellipsoidal Concentrators for Laboratory X-ray Sources: Analytical approaches for optimization," Mar. 22, 2013, Crystallography Reports, vol. 58, No. 2, pp. 355-364.
Yamamoto, "Fundamental physics of vacuum electron sources", Reports on Progress in Physics vol. 69, (2006), pp. 181-232.
Yanagihara et al., "X-Ray Optics," Ch. 3 of "X-ray Spectrometry: Recent Technological Advances," K. Tsuji et al. eds. (John Wiley & Sons, Ltd. Chichester, West Sussex, UK, 2004), pp. 63-131.
Yang et al., "Analysis of Intrinsic Stress in Diamond Films by X-ray Diffraction," Advances in X-ray Analysis, vol. 43 (2000), pp. 151-156.
Yashiro et al., "Distribution of unresolvable anisotropic microstructures revealed in visibility-contrast images using x-ray Talbot interferometry", Phys. Rev. B vol. 84 (2011), 094106.
Yashiro et al., "Hard x-ray phase-imaging microscopy using the self-imaging phenomenon of a transmission grating", Phys. Rev. A vol. 82 (2010), 043822.
Yashiro et al., "Theoretical Aspect of X-ray Phase Microscopy with Transmission Gratings" in International Workshop on X-ray and Neutron Phase Imaging with Gratings, AIP Conf. Proc. vol. 1466, (2012), pp. 144-149.
Yashiro et al., "X-ray Phase Imaging and Tomography Using a Fresnel Zone Plate and a Transmission Grating", in "The 10th International Conference on X-ray Microscopy Radiation Instrumentation", AIP Conf. Proc. vol. 1365 (2011) pp. 317-320.
Yashiro et al., "Efficiency of capturing a phase image using cone-beam x-ray Talbot interferometry", J. Opt. Soc. Am. A vol. 25 (2008), pp. 2025-2039.
Yashiro et al., "On the origin of visibility contrast in x-ray Talbot interferometry", Opt. Express (2010), pp. 16890-16901.
Yashiro et al., "Optimal Design of Transmission Grating for X-ray Talbot Interferometer", Advances in X-ray Analysis vol. 49(3) (2006), pp. 375-379.
Yashiro et al., "X-ray Phase Imaging Microscopy using a Fresnel Zone Plate and a Transmission Grating", in The 10th International Conference on Synchrotron Radiation Instrumentation, AIP Conf. Proc. vol. 1234 (2010), pp. 473-476.
Yashiro et. al., "Hard-X-Ray Phase-Difference Microscopy Using a Fresnel Zone Plate and a Transmission Grating", Phys. Rev. Lett. vol. 103 (2009), 180801.
Yu et al., "Morphology and Microstructure of Tungsten Films by Magnetron Sputtering," Mat. Sci. Forum, vol. 913, pp. 416-423 (2018).
Zanette et al., "Two-Dimensional X-Ray Grating interferometer," Phys. Rev. Lett. vol. 105 (2010) pp. 248102-1-248102-4.
Zeng et al., "Ellipsoidal and parabolic glass capillaries as condensers for x-ray microscopes," Appl. Opt. vol. 47 (May 2008), pp. 2376-2381.
Zeng et al., "Glass Monocapillary X-ray Optics and Their Applications in X-Ray Microscopy," X-ray Optics and Microanalysis: Proceedings of the 20th International Congress, AIP Conf. Proc. vol. 1221, (2010), pp. 41-47.
Zhang et al., "Fabrication of Diamond Microstructures by Using Dry and Wet Etching Methods", Plasma Science and Technology vol. 15(6) (Jun. 2013), pp. 552-554.

\* cited by examiner

MATERIAL MEASUREMENT TECHNIQUES USING MULTIPLE X-RAY MICRO-BEAMS

CROSS REFERENCE TO RELATED APPLICATIONS

The present application claims the priority benefit of U.S. provisional application No. 62/429,760, titled "Material Measurement Techniques Using Multiple X-Ray Micro-Beams," filed on Dec. 3, 2016, the disclosure of which is incorporated herein by reference.

BACKGROUND

X-ray techniques for analysis of various specimens have been used to determine internal structures and compositions. Techniques such as x-ray fluorescence (XRF) analyze the elements present in an object, x-ray diffraction to analyze internal structures of an object, and other techniques may be employed.

To probe the properties of structures on a microscopic scale, one approach is to use a micro-focus x-ray source, imaged with x-ray optics to form a micron-scale x-ray illumination spot, or micro-beam, on the object under examination. When a particular position of the object is exposed, x-rays emerging from the object can be detected, and the properties of the object at that particular position (and only the illuminated position) may be analyzed.

To examine a larger surface and/or volume of an object, it can be useful to use multiple beams rather than a single beam. However, use of multiple beams to interrogate an object in current systems is impractical without a way to identify the signal detected with the individual beam that created it.

What is needed is an improved method for investigating larger surfaces and volumes of an object.

SUMMARY

Figure 1:
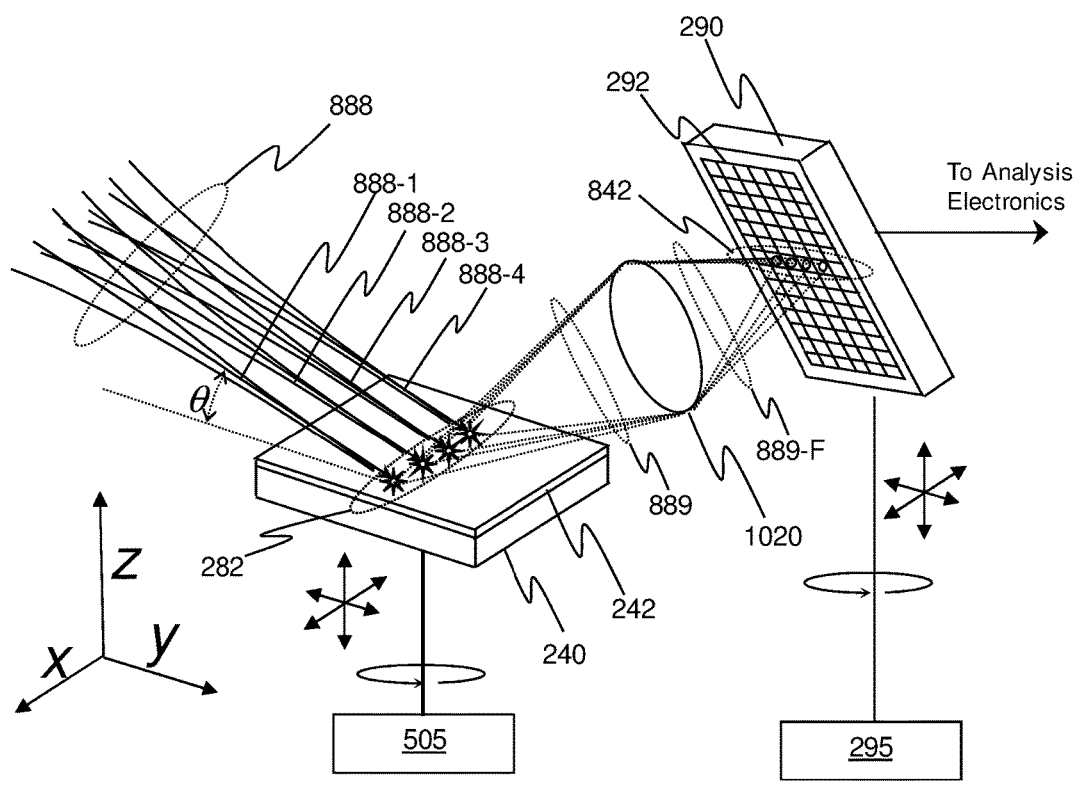
FIG. 1 illustrates an array of x-ray beams used to investigate an object.

The present technology provides an x-ray interrogation system having one or more x-ray beams to interrogate an object of an object. In some instances, a structured source producing an array of x-ray micro-sources can be imaged onto the object. In other embodiments, an x-ray source may illuminate a "beam splitting" grating that produces a set of self-replicating beams in space called a "Talbot Interference pattern" that may be used to illuminate the object. Each of the one or more beams may have a high resolution, such as for example a diameter of about 15 microns or less at the surface of the object. The illuminating one or more micro-beams can be high resolution in one dimension and/or two dimensions, and can be directed at the object to illuminate the object.

In some instances, a method is disclosed which performs spatially resolved x-ray fluorescence analysis. An x-ray excitation beam can be directed upon an object to generate fluorescent x-rays, wherein the x-ray excitation beam includes a planar array of x-ray micro-beams. The individual x-ray micro-beams each having a diameter smaller than 15 microns. The fluorescent x-rays can be imaged with an x-ray imaging system that includes an x-ray imaging optical system and an energy resolving and spatially resolving x-ray detector. The x-ray imaging optical system can collect fluorescent x-rays generated by an object when illuminated by the x-ray excitation beam positioned such that its object plane is coplanar with the plane of the planar array of microbeams within the depth of field of the x-ray imaging optical system. The energy resolving and spatially resolving x-ray detector positioned at the image plane of the x-ray optical imaging system.

In some instances, a method is disclosed which performs spatially resolved x-ray diffraction analysis. An incident x-ray beam is directed upon an object to generate diffracted x-rays. The incident x-ray beam includes an array of x-ray micro-beams, and the individual x-ray micro-beams each have a diameter smaller than 15 microns. Diffraction patterns can be recorded with a spatially resolving x-ray detector positioned a first distance away from the object. Additional diffraction patterns can be recorded by rotating the object relative to the incident beam.

DETAILED DESCRIPTION

The present technology provides an x-ray interrogation system having one or more x-ray beams to interrogate an object. In some instances, a structured source producing an array of x-ray micro-sources can be imaged onto the object. In other embodiments, an x-ray source may illuminate a "beam splitting" grating that produces a set of self-replicating beams in space called a "Talbot Interference pattern" that may be used to illuminate the object. Each of the one or more beams may have a high resolution, such as for example a diameter of about 15 microns or less at the surface of the object. The illuminating one or more micro-beams can be high resolution in one dimension and/or two dimensions, and can be directed at the object to illuminate the object. The incident beam that illuminates the object will have an energy that is greater than or equal to the beam emerging from the object.

The present x-ray interrogation system is discussed herein as interrogating an object, while some references are made to interrogating a sample. It is intended that the terminology of "object" and "sample" is interchangeable.

The x-ray interrogation system may include an imaging system and a detector and may furthermore comprise one or more optics. The use of multiple micro-beams incident upon the sample can result in high resolution obtained at high throughputs, due to simultaneous acquisitions of x-rays from multiple small-diameter microbeams. In this way, the resolution of the system is not related to the overall diameter of the illuminating x-ray beam but instead can be determined by other properties of the imaging system, including the microbeam diameter, the optic(s) focal spot(s), and detector resolution.

The imaging system may include one or more optics. In some instances, the optic can be implemented as an achromatic optic having one or more quadric surfaces. The optic can include a mirror-based Wolter optic, which can include a parabolic mirror followed by a hyperbolic mirror which can focus an array of illuminated x-ray beams at a detector. In some embodiments, one or more x-ray focusing optics may be placed on the illumination beam side to image an array of micro-sources onto the sample.

An imaging x-ray optic may also be included on the detector-side. This optic can be used to image the x-rays emanating due to the interaction of the sample with the microbeams incident upon the sample. The focusing optic and an imaging detector may be aligned such that each detector pixel only records x-rays produced by a single microbeam. In some cases, one single detector pixel is aligned to correspond with x-rays from one single microbeam, and the detector pixel may be substantially larger than microbeam diameter. This enables the use of coarser resolution, higher efficiency detectors. In some other cases, multiple pixels may detect x-rays that correspond to a single micro-beam.

The detector within the x-ray interrogation system can be implemented as a pixel-array detector. A pixel array detector can be a one-dimensional detector, for example for an incident x-ray beam in the shape of a fan or pencil x-ray beam, or a two-dimensional detector. The optical axis for the detector can be approximately perpendicular to the incident optical axis. In some instances, the detector optical axis can be within a range of about 70 degrees to about 110 degrees of the incident optical axis.

The object to be illuminated can be moved to perform tomography analysis on the object. By moving the object and illumination beam relatively, volume mapping can be achieved with fluorescence. For example, directing thin pencil beams incident upon the sample at low angles (e.g. 30 degrees relative to the sample surface) will produce x-rays resulting from the volume interaction of the x-rays from the pencil beams in the sample. A detector system such as an imaging optic coupled to a 2D detector capable of providing depth-resolved information can be used to image the x-rays from the sample. By moving the sample or by moving the illumination beam(s) such that there is relative motion, complete 3-dimensional information can be obtained. Use of multiple x-ray microbeams enables faster acquisition times.

As described in the co-pending U.S. patent application Ser. No. 15/173,711 entitled X-RAY TECHNIQUES USING STRUCTURED ILLUMINATION, enhanced signal-to-noise ratios may be achieved when probing an object under investigation if the signals of multiple x-ray beams are measured recorded individually. And, as described in the co-pending U.S. Provisional Patent Application 62/401,164 entitled X-RAY MEASUREMENT TECHNIQUES USING MULTIPLE MICRO-BEAMS, if the object position is then systematically scanned (for example, in x-and y-coordinates) while being exposed to multiple parallel x-ray beams, a systematic "map" of the properties at the various coordinates where the x-ray beams interact with the object can be created much faster than when using a single x-ray probe to scan the same area. Faster tomographic analysis by rotating and/or scanning the object according to various protocols may also be achieved using parallelized x-ray beams.

Parallelized Micro-Beam for Data Localization.

In some instances, an array of parallel x-ray beams may be used to investigate an object. Both focusing x-ray optics and/or Talbot fringes may be used to form the array of parallel x-ray beams with each having a micron-scale diameter as they illuminate the object being investigated. The x-rays emerging from the object, whether they arise from x-ray fluorescence, x-ray diffraction, or some other x-ray interaction (such as x-ray transmission, x-ray reflection, small angle x-ray scattering (SAXS) and the like) can be attributed to the highly localized properties of the object at the interaction point of the x-ray and the object. Therefore, micron-scale properties of the object may be mapped using micron-scale probe x-ray beams.

FIG. 1 illustrates an array of x-ray beams used to investigate an object. The x-ray beam bundle 888 includes x-ray beams 888-1, 888-2, 888-3, and 888-4, which illuminate an object 240 at an angle θ at a set of illumination points 282. The angle of incidence θ may range between grazing incidence (i.e. a fraction of a degree) to as large as 60° or more for some embodiments. In some instances, the beam width is received at an angle of about 40° with respect to the object surface. As illustrated, the bundle of x-rays beams is arranged in a planar 2-D array, forming a "structured" set x-ray beams focused to a set of one dimensional near-micron-sized spots at the illumination points 282 arranged along the x axis. The structured set of x-ray beams may include two or more beams, and in some instances, may include anywhere between 10-100 beams to several thousand beams. The structured beams may be separated such that when the emerging signal is received by a detector, the signal from focused spots do not overlap significantly. In some instances, the beams in an array of structured x-ray beams may be about 10 to 100 microns apart.

In some instances, the bundle of x-rays 888 may be arranged a 3-D array, or a continuous sheet rather than a structured set of beams, and the illumination spots may be some combination of a one dimensional, two dimensional, and/or three-dimensional array. Also, as illustrated, the object 240 may have a surface coating or layer 242 to be examined. In some instances, the object 240 may be of a single, thick material, and may be any type of object, including those made of non-homogeneous materials or multiple layers.

Figure 2:
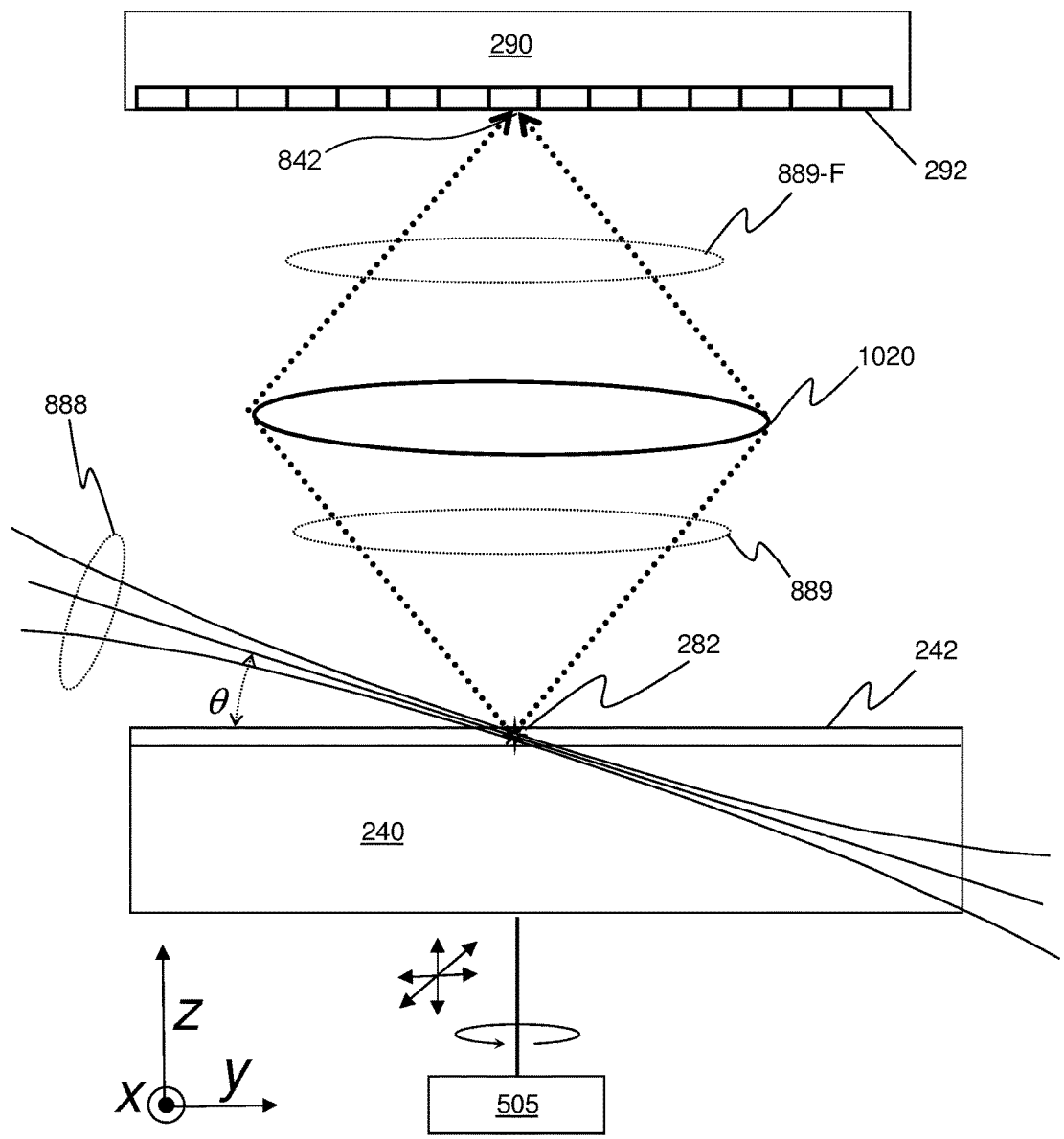
FIG. 2 illustrates a cross-section view of the system of FIG. 1.

FIG. 2 illustrates a cross-section view of the system of FIG. 1. In the embodiment of FIGS. 1-2, the set of illumination points 282 produce x-ray fluorescence 889 from the surface layer 242. These radiated x-rays 889 are collected by an x-ray optical system 1020 to create focused x-rays 889-F. This x-ray optical system 1020 may in some instances comprise one or more x-ray focusing optics.

The x-ray detector 290 can include an array 292 of pixel sensors, and produces electronics signals corresponding to the x-rays impinging on the pixels, which can be further analyzed by electronic means (not shown). The detector pixel size may, in some instances, be between 50 to 200 microns, and may include an array of pixels, such as for example a 2048×2048 grid of pixels. The detector 290 with its pixel array 292 is positioned such that the x-rays emerging from a single one of the illumination points 282 are focused onto a single pixel of the detector. Analyzing the properties of the electronic signal from that single pixel will produce information about just the micro-sized portion of the object 240 illuminated by the corresponding illumination spot.

The pixel-specific data therefore presents information far more localized than an "average" signal from the same pixel would produce if the object 240 were uniformly illuminated. A detector with a larger pixel size (generally much lower in cost) can therefore be used with no "loss" in resolution, as long as the illumination spot is small and the detector is aligned to maintain a unique one-to-one mapping between each illumination spot and a corresponding detector pixel. The alignment may be achieved by positioning an x-ray optic along an axis that is normal to the axis of the incident beam, such that the optic's focal plane coincides with the incident beam. In some instances, the alignment between the optic and the incident beam may be perpendicular or within a range of being perpendicular, such as plus or minus 20° (between 70°-110°). Additionally, the optical axis of the detector can be aligned to be about perpendicular (or, in some instances, between 70°-110°), to the optic focal plane or incident optical axis. In some embodiments, the detector is placed parallel to the sample surface and a monochromatic incident beam illuminates the sample at or below the critical angle of reflection of the x-ray energy such that the system functions as a high resolution total x-ray fluorescence system.

As illustrated in FIG. 1, the object 240 is mounted to a motion control system 505 that may be used to translate the object 240 along x-, y-, and z-axes, as well as rotate the object around various axes. Using the control system 505 to move the object 240 in a pre-programmed manner, for example, systematically collecting data from micron-sized x-ray spots at micron-sized intervals, allows systematic synthesis of high-resolution images of the fluorescence properties of the object 240 with a low-resolution detector. Motion through the distance corresponding to the pitch between x-ray beams along an axis in which x-ray beams are arranged (e.g. the x-axis in FIGS. 1 and 2 ensures that data will be collected by at least one detector pixel for all points along that axis.

The control system 505 may comprise one or more simple translation stages 506, a 5-axis goniometer, or any other known means for systematic object motion known in the art. Motion of the stage may be used to adjust the angle of incidence θ of the x-ray beams by changing the position and orientation of the object 240 relative to the beam(s) 888 while the beam(s) 888 remain fixed in space. Alignment mechanisms 295 may also be provided to adjust the position of the detector pixels to ensure that there is a one-to-one correspondence between illumination spots and detector pixels. Systematic control of the motion of the incident x-ray beam(s), the object and the detector may also be used in some embodiments of the invention. The illumination spots may be scanned in a linear scan, a serpentine scan, a raster scan, or any other pre-determined scanning pattern to allow the collected data to be used to create a "map" of the x-ray properties of the object.

In the system of FIGS. 1-2, x-ray fluorescence from the surface of the object is collected and imaged on the detector. In FIG. 2, the optical system and detector are shown as positioned perpendicular to the surface of the object, as may be practiced in some embodiments. However, various relative orientations of the object, x-ray optical system, and detector may be used, as long as localized fluorescence generation is correlated to the signal from a designated pixel.

X-Ray Optics Considerations.

An x-ray optical system may be employed on the x-ray source side and/or on the detector side. In some instances, the optic system is comprised of one or more optics in which at least a portion of the reflecting surface is paraboloidal or ellipsoidal. In some cases, the optic may have a paraboloidal profile followed by an ellipsoidal profile as in the case for a Wolter-type optic. In many embodiments, the optical system may comprise one or more central beamstops to remove unreflected x-rays transmitted through the center of an axially symmetric optic. The optic system may comprise any x-ray optical elements known to those versed in the art. For example, in some instances, an interrogation system can utilize a confocal optic. In some embodiments, the optic can include an aperture element to remove unreflected x-rays transmitted through the sides of the optic. In some instances, the x-ray optical system may include one or more zone plates. In some instances, the optical system may include a double paraboloid that includes a collimating lens or optic and a focusing lens or optic.

Detector Considerations.

As described above, the pitch of the array detector can be matched to the pitch of the multiple x-ray sources, so that each pixel is positioned to only detect x-rays emerging from the interaction of the object with a single micro-beam, and the cross-talk between pixels due to neighboring micro-beams is minimized. Then, the data collection and final reconstruction of the properties of the object may proceed, knowing that the distinct signals from each pixel need not be further deconvolved. If there is cross-talk between micro-beams and pixels, additional image analysis may be able to remove some of the cross-talk if it can be properly calibrated.

This matching is most straightforwardly achieved if the detector pitch is a 1:1 match to a single micro-beam, i.e. the image of each beam is formed onto one pixel in the detector.

However, smaller detector pitches that are integer fractions of the pitch of the micro-beams (e.g. a 2× reduction in pitch, which would indicate in, for example, a 2-D array, that 4 pixels are positioned to collect the x-rays corresponding to a single micro-beam, or a 3× reduction in pitch, which would indicate 9 pixels resent to detect the x-rays corresponding to each micro-beam) may also be used. This may offer some advantages if the x-rays being detected have some spatial structure.

Likewise, larger detector pitches may also be used if the x-rays emerging from the object under examination are imaged onto the detector using an x-ray optical system that creates a magnified x-ray system. This imaging system may be any of the x-ray optical trains discussed or referred to herein. The optic may be implemented as an achromatic imaging optic that has a field of view equal or greater than the micro-beam diameter. For example, an axially symmetric condenser optic that utilizes glancing incidence reflection to reflect x-rays with inner reflecting surfaces that collects a diverging x-ray beam and then focuses the beam can be designed to create a 1:1 image. In some cases, the optic may be used to produce a magnified image.

The detector may be any one of a number of spatially resolving detectors used to form x-ray images known to those versed in the art such as a detector system comprised of a scintillator screen and visible light optic. In some instances, the detector may be an array x-ray detector that converts spatially dependent x-ray intensity to an electronic signal, including linear detectors, flat panel detectors, energy-resolving array detectors, etc.

One type of commonly used x-ray detector comprises a fluorescent screen or scintillator, such as one comprising a layer of cesium iodide (CsI), thallium doped CsI, yttrium aluminium garnet (YAG) or gadolinium sulfoxylate (GOS), that emits visible photons when exposed to x-rays. The visible photons are then detected by an electronic sensor that converts visible intensity into electronic signals, often with the additional formation of a relay image using visible optics that enlarge and magnify the intensity pattern of the photons emitted by the fluorescent screen.

Although high resolution images by placing the scintillator-type detector near the object can be obtained, the overall thickness of the scintillator and electronic elements must be thin enough so that each detector pixel is collecting only x-rays corresponding to a single micro-beam. This may require a thinner scintillator in some embodiments, reducing the ultimate efficiency.

When using relay optics and a magnified image, the electronic detector need not comprise a high resolution sensor itself, and less expensive larger pixel array detectors may be used. However, when relay optics are used, detection is limited to the field of view collected by the x-ray optics, which may in some cases be only on the order of hundreds of microns. Collecting data on larger areas will then need to be "stitched" together from several exposures.

Detectors with additional structure within each pixel may also be employed as well. For example, if the typical detector pixel is 2.5 microns by 2.5 microns (an area of 6.25 micron$^2$), but the micro-beam diameter is only 1 micron, a detector pixel with a central "spot" of scintillator material slightly larger than 1 micron and positioned to correspond to the position of the image of the micro-beam may be created. With this configuration, all the x-rays from the micro-beam should be detected, while reducing the detection of scattered or diffracted x-rays that would otherwise cause spurious signals if the full area of the detector pixel were to be used. Likewise, pixels in which detector structures (such as scintillator material) are only positioned on the outer portion of the pixel, for example, to only detect x-rays scattered at small angles while not detecting the directly transmitted beam, may also be used for some embodiments.

An aperture element may be placed upstream of the detector to ensure minimal contamination of x-rays from adjacent microbeams. In some cases, this may be a line grid. In other cases, this may be a simple metal film with a hole(s) to form aperture(s), or a patterned material in which certain regions have been thinned or comprise materials with low x-ray absorption properties (e.g. carbon fiber, aluminum, etc.) to provide regions that transmit more x-rays. The size and shape of the aperture may be selected to correspond to the size and shape of the region of interest in the object under examination. The dimensions of the aperture may be as small or smaller than the point spread function of an optical train, and may be as small as 0.1 micrometers, or may be larger if larger areas of the object are under examination. The aperture may have the shape of a circle, a slit, a square, a cross, a diamond, an annulus, or a custom designed shape to match particular predetermined shapes that may be anticipated to be found in the object.

3D X-Ray Acquisition Using Multi-Beams.

Figure 3:
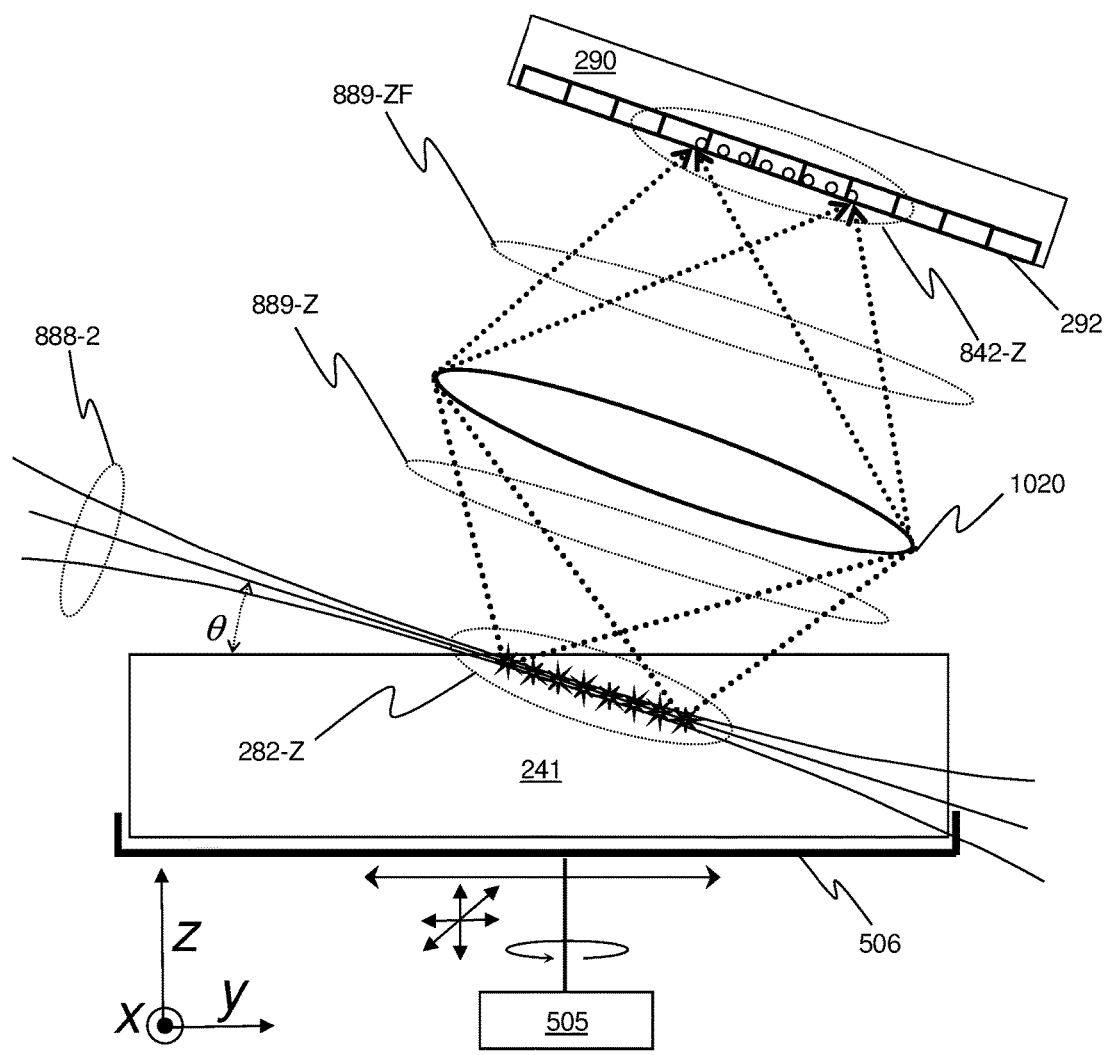
FIG. 3 illustrates an x-ray fluorescence generated from different depths of an object being interrogated.

FIG. 3 illustrates x-rays generated from different depths of an object being interrogated with a microbeam. In this example, fluorescent x-rays are being detected.

FIG. 3 illustrates a cross-section view of an arrangement similar to FIGS. 1-2, but with the detector system positioned to provide depth-resolved imaging. Each of the discrete x-ray beams (such as 888-1, 888-2, etc.) produce an illumination zone 282-Z as the x-ray beam enters the object. Fluorescence x-rays 889-Z emerging from the illumination zone 282-Z are collected by an x-ray optical system 1020, creating focused x-rays 889-ZF that form an image 842-Z of the illumination zone at the detector 290.

X-ray fluorescence 889-Z is collected by the x-ray optical system 1020 and is focused as a line on multiple pixels in the detector 290. The y-axis (and, to the degree that pixels along the direction of propagation can be correlated with the depth into the object using the angle of incidence θ, the z-axis) information is distributed over several pixels, and resolution is in part limited by the y-axis pixel spacing of the detector.

As illustrated in FIG. 3, the x-ray optical system 1020 and detector 290 are positioned at an angle to the surface of the object 241, so that they "view" the line of x-ray fluorescence in the illumination zone 282-Z from an angle perpendicular or near perpendicular to the direction of propagation of the x-ray beam, for example between 70-110 degrees, thereby allowing the image 842-Z of the illumination zone 282-Z to be more uniformly in focus. In this embodiment, the x-ray optical system is comprised of one or more x-ray imaging optics.

As was described in the previous embodiment, the object 241 in FIG. 3 is mounted to a motion control system 505 (in this example, with a mount 506) that may be used to translate the object along x-, y-, and z-axes, as well as rotate the object around various axes. Using the control system 505 to move the object 240 in a pre-programmed manner, for example, systematically collecting data from micron-sized x-ray spots at micron-sized intervals, allows systematic synthesis of high-resolution images of the fluorescence properties of the object 241 with detector having lower-resolution, at least in the x-axis. Rotation of the object by 90° allows the portions of the object that were previously aligned along the y-axis (at a resolution dictated by the pixel resolution) to now be positioned along the x-axis (thereby allowing high resolution, localized x-ray fluorescence data collection along this axis as well). In some instances, the rotation is such that the rotation axis intersects the incident x-ray beam within the object.

Figure 4:
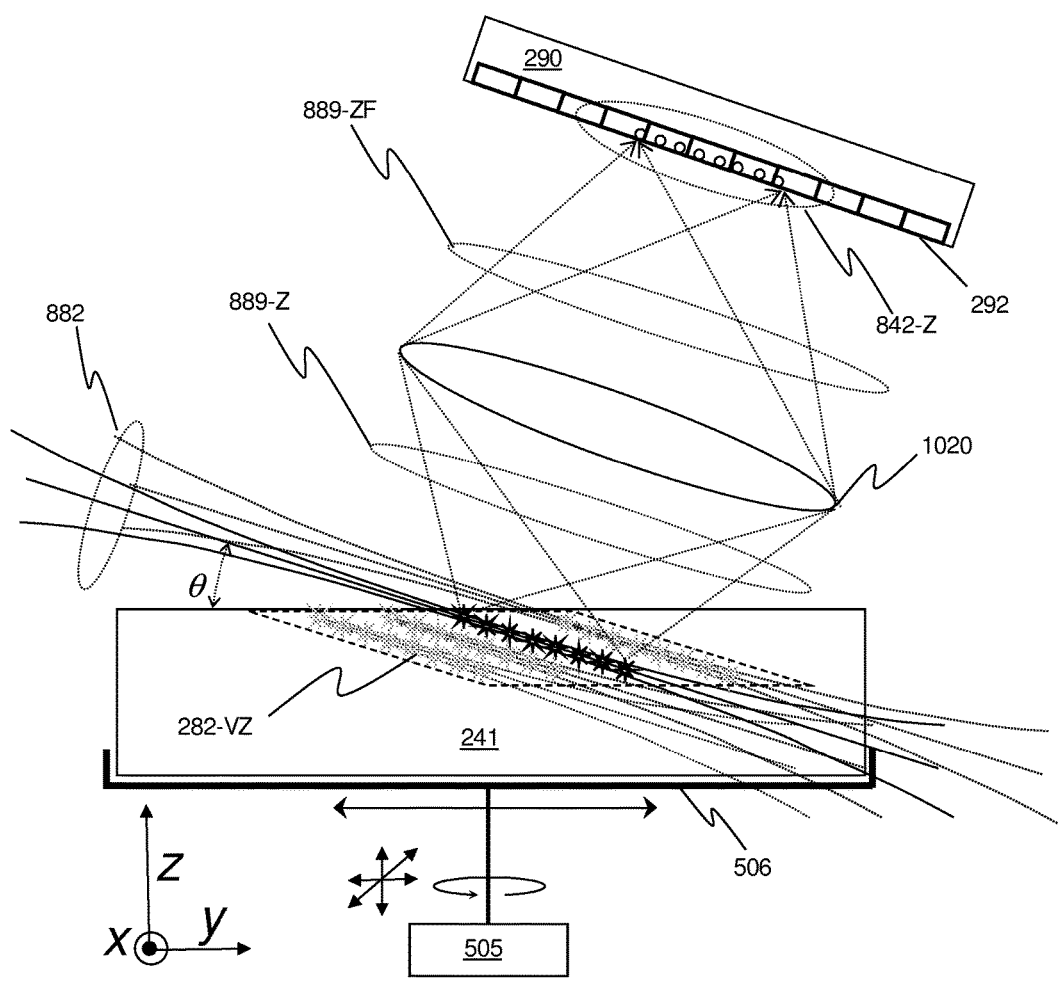
FIG. 4 illustrates an object under interrogation under a three-dimensional volume.

FIG. 4 illustrates an object under interrogation under a three-dimensional volume. As illustrated in FIG. 4, moving and/or rotating the object along the y-axis allows the sweeping of the x-ray illumination beams over a 3-D volume of the object (shown as 282-VZ). With the suitable correlation of the position of the object and detector over a range of positions and rotations, high-resolution 3-D information about the x-ray fluorescence, and therefore the 3-D composition, of the object may be determined.

Note that, as illustrated in FIG. 4, the x-ray illumination beam(s) 888, x-ray optical system 1020, and the detector 290 will generally be pre-aligned and relatively stationary with each other, while the object 241 mounted in a stage 506 is moved in a pre-programmed manner to allow the illuminating x-rays to illuminate different portions of the object. Algorithms to synchronize the motion (rotations and/or translations) of the stage 506 holding the object 241 that allow the signal from a pixel of the detector to be correlated to the portion of the object being imaged (which may also include convolution with the illuminating x-ray beam dimensions) can provide a complete sweep of the volume under examination and can be derived from the various geometric factors of the arrangement. In some alternative embodiments, the illumination beam, optical system, and detector system may move while the object remains stationary.

Multi-Beam X-ray Diffraction.

Figure 5:
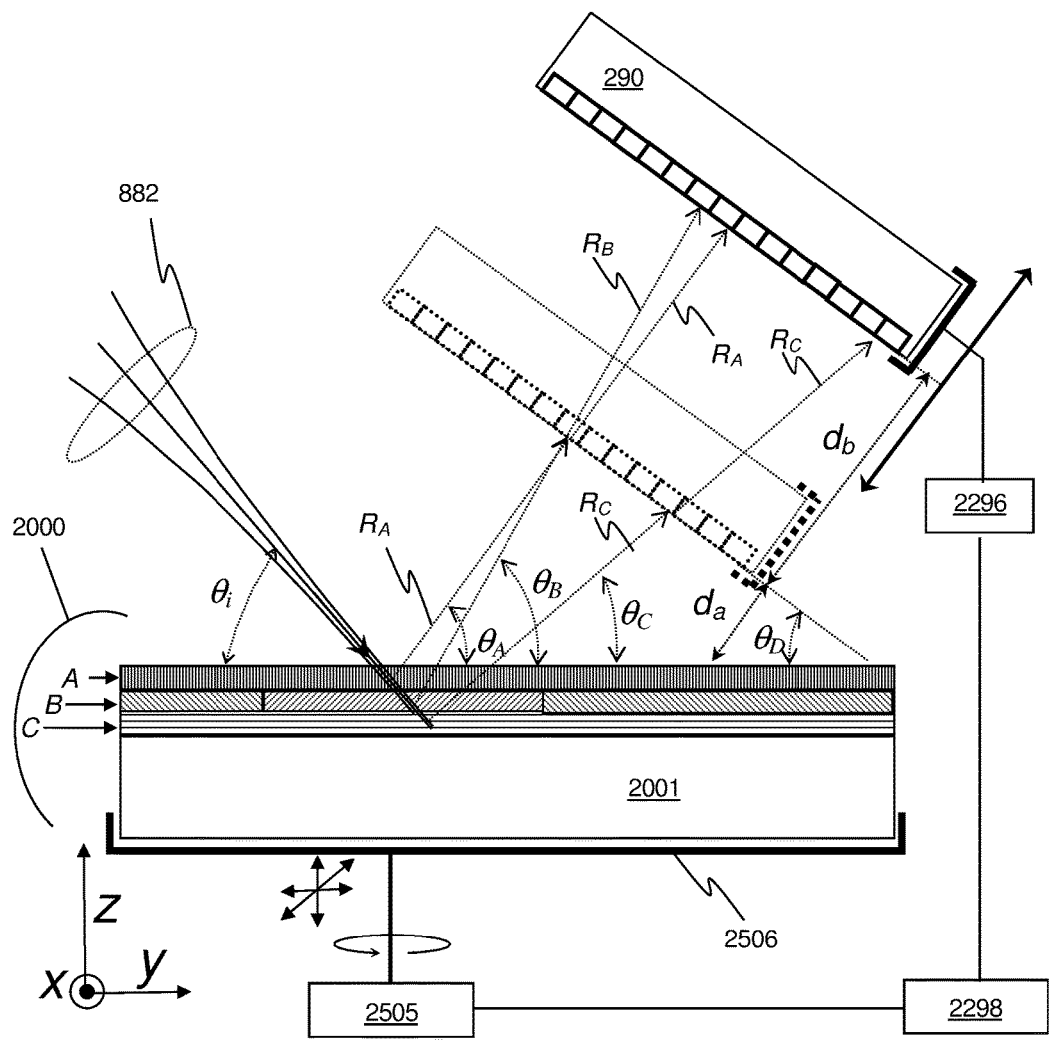
FIG. 5 illustrates utilizing x-ray diffraction for interrogating an object.

FIG. 5 illustrates utilizing x-ray diffraction for interrogating an object. X-ray diffraction can be used to determine information about the structure of an object, and can be interpreted using an illumination arrangement comprising multiple x-ray beams like that illustrated in FIG. 1.

As shown in the schematic cross-section illustration of FIG. 5, the x-rays diffracted emerge at specific angles related to the local structure of the material from the structures. An x-ray imaging optical system will generally have a small acceptance aperture, and will not collect all the diffracted x-rays. So, for x-ray diffraction measurements, direct detection of the diffracted x-rays is achieved without an imaging optic, but instead by using an array x-ray detector positioned some distance away from the object.

It should be noted that some x-ray fluorescence may also be generated by the exposure of the object to illuminating x-rays, and that a detector simply positioned in space at some distance from the object will detect not only diffracted x-rays, but any fluorescence x-rays that also fall on the detector. The fluorescence x-rays, however, will tend to have a lower energy than the diffracted x-rays, and so an energy discriminating detector may be used to identify which signals arise from fluorescence and remove them. An x-ray cutoff filter may also be placed between the object and the detector (not illustrated in FIG. 5) to absorb the fluorescence x-rays while allowing higher energy diffracted x-rays to be transmitted. Objects comprising iron (Fe), for example, may produce strong x-ray fluorescence that needs to be filtered or otherwise mitigated to prevent signals from the detection of iron fluorescence from saturating the x-ray detector.

The object 2000 of FIG. 5 comprises a substrate 2001 and 3 layers: A, B, and C, each marked with a different fill pattern to symbolically represent different physical structures within (with layer B additionally being shown as being a non-homogeneous layer).

One or more x-ray beams 882 converge onto the object 2000 at an angle of incidence $\theta_i$ with a predetermined beam diameter at the object. The beam(s) may be an array of focused beams or a Talbot interference pattern, as was discussed in the previous examples, or some other configuration producing points of localized illumination at the object 2000. The angle of incidence $\theta_i$ may range between grazing incidence (i.e. a fraction of a degree) to as large as 60° or more for some embodiments. As the beam or beams 882 interact with the various structures in the object, diffracted x-rays at various angles may emerge. These may be due to Bragg reflections from the atomic layers making up the local crystal structure, or other scattering effects from within the material.

As illustrated in FIG. 5, each of the layers, A, B, and C, diffracts x-rays from the incident beam 882. For this illustration, only a single beam is shown emerging from each of the layers (ray $R_A$ at angle $\theta_A$ from layer A, ray $R_B$ at angle $\theta_B$ from layer B, ray $R_C$ at angle $\theta_C$ from layer C), although in practice a plurality, for example several to many, diffracted rays of various intensities and at a plurality, for example several to many, different angles will emerge from each material structure.

As is well known in the art of x-ray diffraction, the relationship between incident angles, diffracted angles, and diffracted x-ray intensity can be used to infer information about the structure of the material diffracting the x-rays (inferring spacing and orientation of atomic planes, etc.). A detector placed at a known distance from the object (shown as a distance $d_a$ and oriented at an angle $\theta_D$ relative to the surface of the object) allows the inference of many of these variables. The diffracted x-rays can be used, for example, to generate crystallographic information for the object.

However, a single measurement of the intensity of diffracted spots at a particular distance from the object leaves some ambiguity as to the exact position of origin within the object. And, as shown in FIG. 5, when the detector is placed at a position in which two of the diffracted rays happen to be coincident (as shown for rays $R_A$ and $R_B$) then an x-ray intensity signal from the pixels of the detector cannot be unambiguously assigned to have an origin at any particular position.

This can be addressed by moving the detector to a second position and making another set of measurements. In most cases, if the separation distance $d_b$ between the first position and the second position is known and well chosen, the trajectory of rays from the object, the first position, and the second position can be unambiguously defined, and the position of origin within the object for a given ray can be determined. In some cases, making still additional measurements at additional positions may further add accuracy and reliability to the measurement.

As was described in the previous embodiments, the object 2000 in FIG. 5 is also mounted to a motion control system 2505 (in this example, with a mount 2506) that may be used to translate the object along x-, y-, and z-axes, as well as rotate the object around various axes. Hence, moving the object and x-ray excitation beam relatively may allow for diffraction x-rays to be determined and structural properties of the object to be determined. Using the control system 2505 to move the object 2000 in a pre-programmed manner, for example, systematically collecting diffraction data from micron-sized x-ray spots at micron-sized intervals at a plurality of distances and at known relative angles allows the structural properties of the object 2000 to be determined. Motion of the stage 2506 may be used to adjust the angle of incidence $\theta_i$ of the x-ray beam(s) 882 by changing the position and orientation of the object 2000 relative to the beam(s) 882 while the beam(s) 882 remain fixed in space. By adjusting the angle of incidence, x-rays additional diffraction angles or at higher orders may also be detected.

In some instances, the object and incident x-ray beam can be moved, relatively to each other, so that diffraction information is gathered from a larger volume of the object.

Also shown in FIG. 5 are a position and angle controller 2296 for the detector 290, and an additional controller 2298 to coordinate the motion of the object 2000 and the detector 290.

As in the previously described embodiments, the array of beams that illuminate the object 2000 can be a single beam, a single planar array of beams, a 2-D array of beams, or a 3-D array of beams, and can be structured with a beam diameter on a micron-scale. The arrays can be created by imaging a structured x-ray source using x-ray imaging optics, created as a set of Talbot interference fringes, or some by other means that may be known to those skilled in the art. However, one consideration for diffractive measurements is that the separation between the x-ray beam illumination spots should be large enough to allow the clear calculation of the position of origin and trajectory of the diffracted beam.

Figure 6:
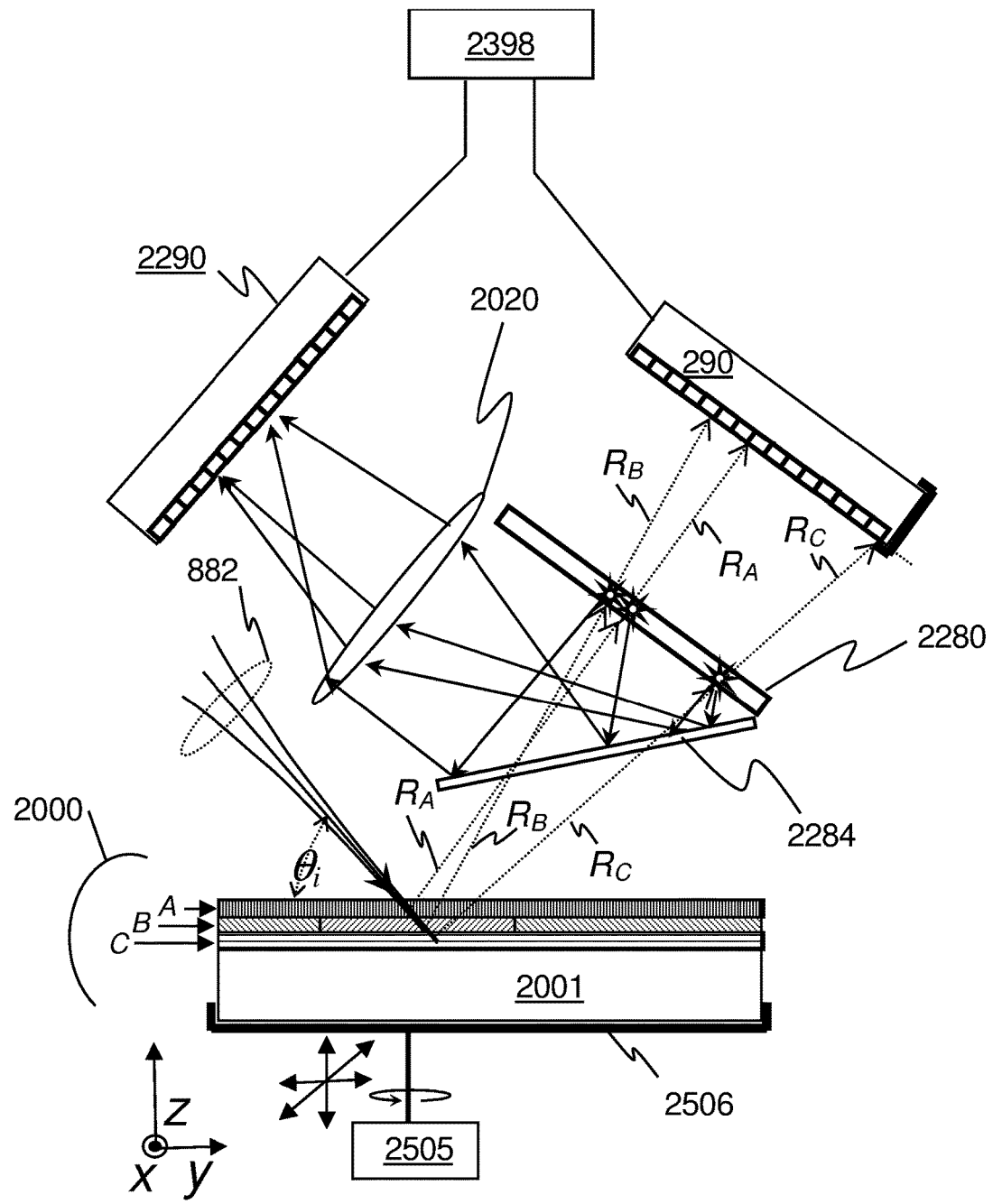
FIG. 6 illustrates an interrogation system having multiple detector systems.

FIG. 6 illustrates an interrogation system having multiple detector systems. In this embodiment, two detector systems are simultaneously employed. The first detector system comprises a first spatially-resolved detector 290 (typically a 2-D array x-ray detector) placed at a first known position relative to the incident x-rays. This identifies one set of positions for the various diffracted rays.

Between the object 2000 and first detector 290, a scintillator 2280 is placed at a second known position relative to the incident x-rays. The scintillator absorbs some of the diffracted x-rays and emits visible photons, generally with the visible photon intensity in proportion to the x-ray intensity. A thin mirror 2284 for visible light (and relatively transparent to x-rays) is placed to reflect the visible light from the scintillator and, using an optical imaging system 2020, form an image of the scintillator onto a visible photon detector 2290. If the visible photon detector 2290 is an array detector, and the relative positions and angles of the visible photon detector 2290, the scintillator 2280, the x-ray array detector 290 are all known relative to the object 2000 and the incident x-ray beam(s) 882, the relative angles and x-ray intensities of the diffracted rays can be inferred using information from the first detector 290 and the second detector simultaneously by means of an analysis algorithm in an analysis system 2398 without physical motion of a detector.

Figure 7A:
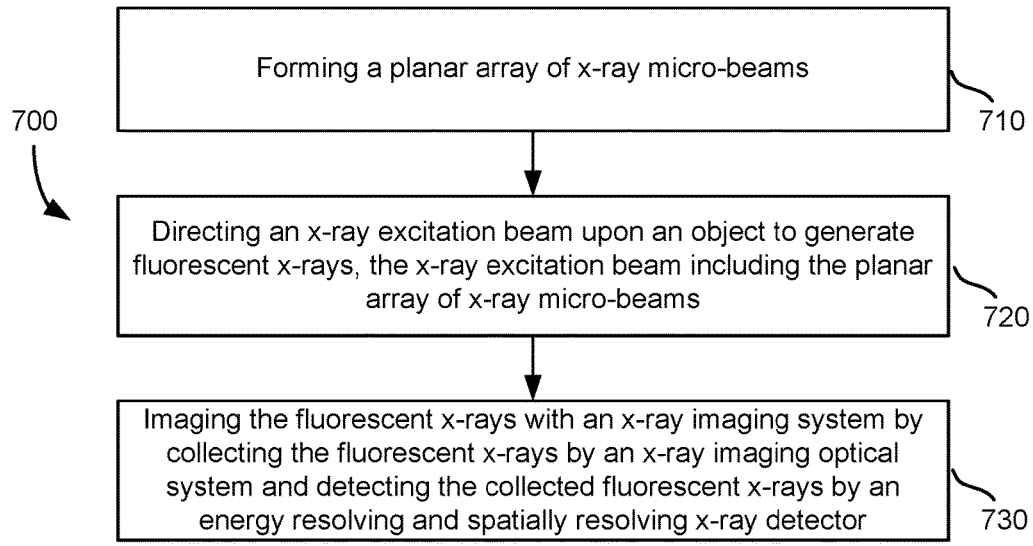
FIG. 7A illustrates a method for interrogating an object using fluorescence x-rays.

FIG. 7A illustrates a method 700 for interrogating an object using fluorescence x-rays. The method begins at step 710 with forming a planar array of x-ray micro-beams. The x-ray micro-beams may be formed by an array of x-ray micro-sources imaged by an x-ray imaging optic, transmitting x-rays from at least one source through a plurality of apertures, or variations of these techniques. An x-ray excitation beam is directed upon an object to generate fluorescent x-rays, wherein the x-ray excitation beam includes a planar array of x-ray micro-beams, at step 720. The individual x-ray micro-beams can each have a diameter smaller than 15 microns, and the planar array of x-ray micro-beams has an angle of incidence less than 70 degrees with respect to the object surface.

The fluorescent x-rays are imaged with an x-ray imaging system at step 730. The x-ray imaging system can include an x-ray imaging optical system and an energy resolving and spatially resolving x-ray detector. The x-ray imaging optical system collects fluorescent x-rays generated by an object when illuminated by the x-ray excitation beam positioned such that its object plane is coplanar with the plane of the planar array of microbeams within the depth of field of the x-ray imaging optical system. The energy resolving and spatially resolving x-ray detector is positioned at the image plane of the x-ray optical imaging system.

Figure 7B:
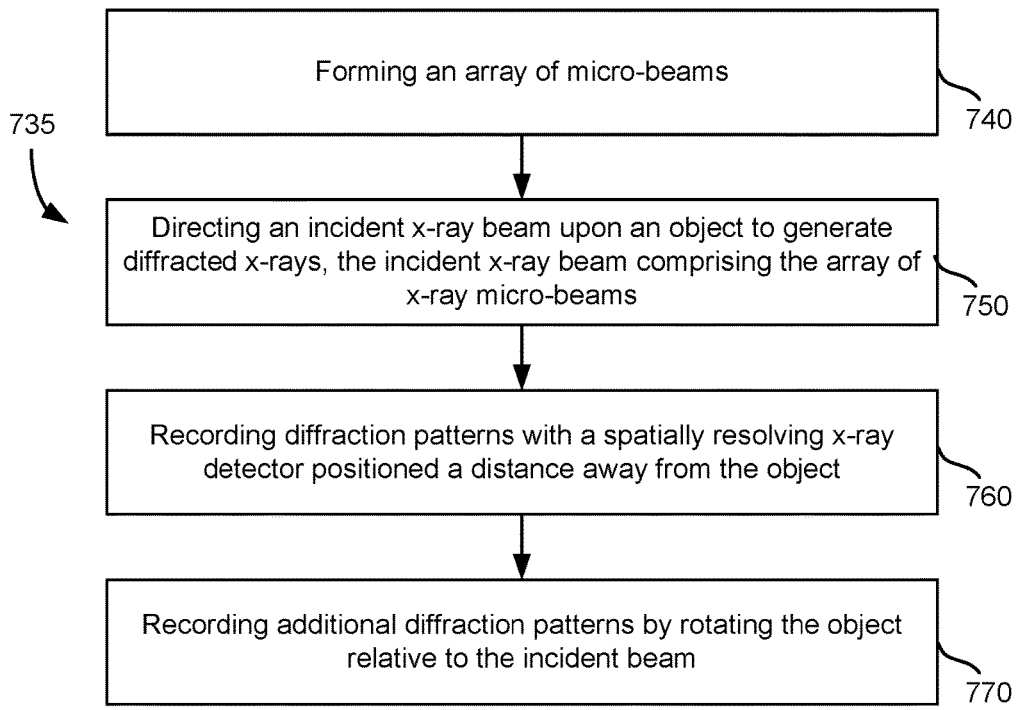
FIG. 7B illustrates a method for interrogating an object using diffraction x-rays.

FIG. 7B illustrates a method 735 for interrogating an object using diffraction x-rays. An array of micro-beams is formed at step 740. The micro-beam array can be a two-dimensional array of a planar array of x-ray micro-beams, and the micro-beam array can be formed by an array of x-ray micro-sources imaged by an x-ray imaging optic, by transmitting x-rays from at least one source through a plurality of apertures, and/or by creating a Talbot interference pattern.

An incident x-ray beam is directed upon an object at step 750 to generate diffracted x-rays. The incident x-ray beam includes an array of x-ray micro-beams, and the individual x-ray micro-beams each can have a diameter smaller than 15 microns. The diffraction patterns can be recorded with a spatially resolving x-ray detector positioned a distance away from the object at step 760. Additional diffraction patterns can be recorded at step 770 by rotating the object relative to the incident beam. The rotation is such that the rotation axis intersects the incident x-ray beam within the object.

In some instances, diffraction patterns may be recorded at multiple distances away from the object to establish the direction of a diffracted x-ray. For example, at step 760, the spatially resolving x-ray detector can record diffraction patterns at a first distance away from the object and again when the detector is at a second distance away from the object. In another example, a first detector may record diffraction patterns at a first distance from the object and a second detector may record diffraction patterns at a second distance from the object, where the first detector is a partially transmitting detector.

Additional Concepts

The illuminating x-rays may be of any energy, but certain embodiments may use x-rays with a mean energy between 3 keV and 70 keV. Likewise, some embodiments may use x-rays for which the x-ray spectrum has an energy bandwidth of ±20%.

The dimensions of the x-ray beams as they interact with the object have been described generally as "micron-sized" beams, but x-ray beams with diameters as small as 100 nm or anywhere in the range from 100 nm to 10 microns may also be used in some embodiments. X-ray beams with varying dimensions (i.e. non-uniform beam diameters) may also be used in some embodiments.

The multiple x-ray beams may be produced in any of several ways. For instance, by an imaging x-ray optic placed downstream of an x-ray source with a target of separated micro-emitters. In other embodiments, this may be produced with an x-ray source with a linear or 2D array of apertures placed in front of it. In still other embodiments, this can be achieved by obtaining the Talbot effect using interferometry. Still other embodiments may comprise multiple discrete micro x-ray sources.

In some instances, an x-ray imaging optic placed upstream from the sample and an x-ray imaging optical system placed between the sample and the detector may each include one or more optics having one or more interior surface coatings and/or layers. In some embodiments, the coating can be of materials that have a high atomic number, such as platinum or iridium, to increase the critical angle of total external reflection. In some instances, the coating may be a single layer coating. In some instances, multilayer coating comprised of many layers (e.g., several hundred) of two or more alternating materials. Layers may be of uniform thickness or may vary in thickness between layers or within a single layer, such as in the cases of depth-graded multilayers or laterally-graded multilayers. The multilayer coating will narrow the bandwidth of the reflected x-ray beam and can serve as a monochromator. The materials used in the multilayer coating may be of any known to those versed the art.

The x-ray source producing the array of x-ray beams may also comprise an x-ray filter or monochromator (optional) to provide x-rays of a specific energy or a specific distribution of energies. Embodiments in which x-ray exposure is carried out using different x-ray energies at different times may also be designed, inferring information about the object from the spectral response of the x-ray signals as correlated with the exposure energy.

It should also be noted that, although embodiments directed towards fluorescence and diffraction have been separately described (one illustrated using an embodiment having imaging optics, the other illustrated using a detector positioned to detect direct diffraction from the object without imaging), systems in which both fluorescence and diffraction are detected, either with the same, energy resolving detector, or with two different detectors, simultaneously or in sequence, are possible as well. Embodiments incorporating x-ray fluorescence and/or x-ray diffraction along with other x-ray measurement techniques (e.g. x-ray transmission, x-ray reflection, small-angle x-ray scattering, etc.) are also possible.

We claim:

1. A method to perform spatially resolved x-ray fluorescence analysis, comprising:
    directing an x-ray excitation beam upon an object to generate fluorescent x-rays, the x-ray excitation beam comprising a planar array of x-ray micro-beams, the individual x-ray micro-beams each having a diameter smaller than 15 microns at a surface of the object; and
    imaging the fluorescent x-rays with an x-ray imaging system that includes an x-ray imaging optical system and an energy resolving and spatially resolving x-ray detector, the x-ray imaging optical system collecting fluorescent x-rays generated by the object when illuminated by the x-ray excitation beam, the x-ray imaging optical system positioned such that an object plane of the x-ray imaging optical system is coplanar with the plane of the planar array of micro-beams within a depth of field of the x-ray imaging optical system, the energy resolving and spatially resolving x-ray detector positioned at an image plane of the x-ray imaging optical system.

2. The method of claim 1, wherein the planar array of x-ray micro-beams is formed by an array of x-ray micro-sources imaged by an x-ray imaging optic.

3. The method of claim 1, wherein the planar array of x-ray micro-beams is formed by transmitting x-rays from at least one source through a plurality of apertures.

4. The method of claim 1, wherein the x-ray imaging optical system includes a zone plate.

5. The method of claim 1, wherein the x-ray imaging optical system includes a Wolter optic.

6. The method of claim 1, wherein the x-ray imaging optical system includes a collimating lens and a focusing lens.

7. The method of claim 1, wherein the x-ray imaging optical system includes an x-ray optic having an inner surface with at least one portion of the inner surface corresponding to a portion of a quadric profile.

8. The method of claim 7, wherein the quadric profile is paraboloidal.

9. The method of claim 1, wherein the planar array of x-ray micro-beams has an angle of incidence less than 70 degrees with respect to the surface of the object.

10. The method of claim 1, wherein the x-ray imaging optical system is achromatic.

11. The method of claim 1, wherein the x-ray imaging optical system includes one or more quadric surfaces.

12. The method of claim 1, further comprising adjusting at least one of the object and the x-ray excitation beam such that there is relative motion between the object and the x-ray excitation beam and collection x-ray fluorescence from a volume of the object.

13. A method to perform spatially resolved x-ray diffraction analysis, comprising:
    directing an incident x-ray beam upon an object to generate diffracted x-rays, the incident x-ray beam comprising an array of x-ray micro-beams, the individual x-ray micro-beams each having a diameter smaller than 15 microns at a surface of the object;
    recording diffraction patterns with a spatially resolving x-ray detector positioned a first distance from the object; and
    recording additional diffraction patterns by rotating the object relative to the incident x-ray beam.

14. The method of claim 13, wherein said rotation comprising rotating the object about a rotation axis that intersects the incident x-ray beam within the object.

15. The method of claim 13, further comprising analyzing the recorded diffraction patterns to generate crystallographic information for the object.

16. The method of claim 13, wherein the array of x-ray mirco-beams is a two-dimensional array of x-ray micro-beams.

17. The method of claim 13, wherein the array of x-ray micro-beams is a planar array of x-ray micro-beams.

18. The method of claim 13, wherein the array of x-ray micro-beams is formed by an array of x-ray micro-sources imaged by an x-ray imaging optic.

19. The method of claim 13, wherein the array of x-ray micro-beams is formed by transmitting x-rays from at least one source through a plurality of apertures.

20. The method of claim 13, wherein the array of x-ray micro-beams is formed by creating a Talbot interference pattern.

21. The method of claim 13, further comprising:
    moving the spatially resolving x-ray detector to a position at a second distance from the object; and
    imaging the diffracted x-rays with the spatially resolving x-ray detector positioned at the second distance.

22. The method of claim 13, further comprising positioning an x-ray filter upstream from the spatially resolving x-ray detector to reduce undiffracted x-rays.

23. The method of claim 13, further comprising adjusting at least one of the object and the incident x-ray beam such that there is relative motion between the object and the incident x-ray beam, and gathering diffraction information from a volume of the object.

* * * * *

UNITED STATES PATENT AND TRADEMARK OFFICE
CERTIFICATE OF CORRECTION

PATENT NO. : 10,247,683 B2
APPLICATION NO. : 15/829947
DATED : April 2, 2019
INVENTOR(S) : Wenbing Yun et al.

It is certified that error appears in the above-identified patent and that said Letters Patent is hereby corrected as shown below:

Column 13, Line 39, in Claim 12, change "collection" to --collecting--.

Column 14, Line 9 (approx.), in Claim 14, change "rotation" to --rotating--.

Column 14, Line 16 (approx.), in Claim 16, change "mirco-beams" to --micro-beams--.

Signed and Sealed this
Sixteenth Day of July, 2019

Andrei Iancu
*Director of the United States Patent and Trademark Office*